(12) United States Patent
Jin et al.

(10) Patent No.: US 6,764,837 B1
(45) Date of Patent: Jul. 20, 2004

(54) AGROBACTERIUM TUMEFACIENS RPOA GENE

(75) Inventors: Shouguang Jin, Gainesville, FL (US); Scott M. Lohrke, Beltsville, MD (US); Konstantin Severinov, Highland Park, NJ (US); Marie Chow, Little Rock, AR (US)

(73) Assignees: Board of Trustees of the University of Arkansas, Little Rock, AR (US); Rutgers the State University of New Jersey, Piscataway, NJ (US)

(*) Notice: Subject to any disclaimer, the term of this patent is extended or adjusted under 35 U.S.C. 154(b) by 0 days.

(21) Appl. No.: 09/958,940

(22) PCT Filed: Apr. 14, 2000

(86) PCT No.: PCT/US00/10014

§ 371 (c)(1),
(2), (4) Date: Jan. 16, 2002

(87) PCT Pub. No.: WO00/63413

PCT Pub. Date: Oct. 26, 2000

Related U.S. Application Data

(60) Provisional application No. 60/134,206, filed on May 14, 1999, and provisional application No. 60/129,682, filed on Apr. 6, 1999.

(51) Int. Cl.[7] .................. C12N 15/09; C12N 15/00; C12N 15/86; C12N 1/20; C07H 21/04
(52) U.S. Cl. .................. 435/69.7; 435/69.1; 435/325; 435/252.3; 435/320.1; 435/471; 536/23.1; 536/23.4; 536/24.1
(58) Field of Search .................. 435/69.1, 325, 435/252.3, 320.1, 235.1, 471, 69.7; 536/23.1, 23.4, 24.1

(56) References Cited

FOREIGN PATENT DOCUMENTS

WO    WO 98/24891 A1    6/1998

OTHER PUBLICATIONS

Berendsen, Herman. Science, Oct. 1998, vol. 282, pp. 642–643.*

Lohrke, et al. Journal of Bacteriology, Jun. 2001, vol. 183, No. 12, pp. 3704–3711.*

Lohrke et al., Transcriptional Activation of *Agrobacterium tumefaciens* Virulence Gene Promoters in *Escherichia coli* Requires the *A. tumefaciens* rpoA Gene, Encoding Alpha Subunit of RNA Polymerase. Journal of Bacteriology, Aug. 1999, vol. 181, No. 15, pp. 4533–4539.

Steffen et al., Hybrid *Bordetella pertussis–Escherichia coli* RNA Polymerases: Selectivity of Promoter Activation, Journal of Bacteriology, Mar. 1998, vol. 180, No. 6, pp. 1567–1569.

Boylan et al., Gene Encoding the Alpha Core Subunit of *Bacillus subtilis* RNA Polymer Cotranscribed with the Genes for Initiation Factor 1 and Ribosomal Proteins B, S13, S11 and L17, Journal of Bacteriology, May 1989, vol. 171, No. 5, pp. 2553–2562, especially Figure 2.

Altschul et al., Gapped BLAST and PSI–BLAST: A new generation of protein database search programs, Nucleic Acids Res., 1997, pp. 3389–3402, vol. 25, No. 17, Oxford University Press.

Borukhov et al., Recombinant *Escherichia coli* RNA Polymerase: Purification of Individually Overexpressed Subunits and in Vitro Assembly, Protein Expression and Purification, 1993, pp. 503–511, vol. 4, Public Health Research Institute, New York City.

* cited by examiner

*Primary Examiner*—Gerry Leffers
(74) *Attorney, Agent, or Firm*—Foley & Lardner

(57)    ABSTRACT

The present invention is directed to a method for expression of at least one heterologous gene in a host cell comprising transforming a host cell with at least one nucleic acid construct comprising a complete α subunit of an RNA polymerase or a portion thereof of a hybrid nucleic acid containing a portion of the α subunit of an RNA polymerase obtained from the same genus as the heterologous gene, and transforming the host cell, with at least one heterologous gene; and culturing the transformed host cell. The present invention further is directed to nucleic acid molecules used in the present method, vectors containing these nucleic acid molecules, and host cells containing the nucleic acid molecules. The nucleic acid encoding the α subunit of an Agrobacterium RNA polymerase and the corresponding amino acid sequence and portions thereof is disclosed.

18 Claims, 6 Drawing Sheets

FIG. 2A

| | |
|---|---:|
| MIQKNWQELIKPNKVEFTSSSRTKATLVAEPLERGFGLTLGNALRRVLLS | 50 |
| SLRGAAVTAVQIDGVLHEFSSIPGVREDVTDIVLNIKEIAIKMDGDDSKR | 100 |
| MVVRKQGPGSVTAGDIQTVGDIEILNPDHVICTL.DEGAEIRMEFTVNNG | 149 |
| KGYVPAE—RNRAEDAPIGLIPVDSLYSPVKKVSYKVENTREGQVLDYD | 196 |
| KLIMTIETNGSVSGEDAVAFAARILQDQLGVFVNFDEPQKEAEEESVTEL | 246 |
| AFNPALLKKVDELELSVRSANCLKNDNIVYIGDLIQKTEAEMLRTPNFGR | 296 |
| KSLNEIKEVLASMGLHLGMEVPAWPPENIEDLAKRYEDQY | 336 |

FIG. 2B

```
   1 aacacggcat gaagtcgctt gaagtcgaag tttgcggtcc gggttccggt cgtgaatcgg
  61 cacttcgcgc tctgcaggct gccggtttca tgatcacttc cattcgcgac gccgatcccg
 121 cacaacggtt gccgtccgcg caagaagcgc cgcgtctgac gcgaccgtgg ttcggaaatt
 181 ccgcctttcc ttcggtctgg cggaattttc gtgtatctgg cgtgtgcgcg tcgatttcga
 241 tcgacggact tgcgctcaag aacccactga tgaaccactg aattaggttc ctctcggtgt
 301 tttcatgctc ggtccgtcac gattggatgg tggcggcgaa cggaaggttt aaagatgatt
 361 cagaagaact ggcaggaact tatcaagccg aacaaggtcg agttcacctc gtccagccgc
 421 accaaggcaa ctctggttgc cgagccgctg gagcgtggtt tcggtcttac cctcggcaac
 481 gcgctgcgcc gcgttctgtt gtcttctctg cgtggtgccg ctgtaacggc cgtgcagatc
 541 gacggtgtcc tgcacgaatt ctcctccatc cccggcgttc gggaagatgt gacggatatc
 601 gtgctcaaca tcaaggaaat cgccatcaag atggatggtg acgattccaa gcgcatggtc
 661 gtgcgcaagc agggtccggg ttcggtaacc gctggtgaca tccagacggt tggcgacatc
 721 gagatcctga accccgacca cgtgatctgc acgctcgatg aaggcgctga aatccgcatg
 781 gaattcaccg tcaacaacgg caagggttac gtaccggctg agcgcaaccg cgcggaagat
 841 gccctatcg gcctcattcc ggtggacagc ctctattctc cggtcaagaa agtgtcctac
 901 aaggtggaaa acacccgtga aggtcaggtt ctcgactatg acaagctgat catgacgatc
 961 gagaccaacg gttcggtttc cggcgaagac gccgttgcct tcgccgctcg cattcttcag
1021 gaccagctgg gcgtcttcgt caacttcgac gagccgcaga aggaagcaga agaagaatcg
1081 gttactgaac tcgcgttcaa cccggcgctt ctcaagaagg tcgacgagct cgaactgtca
1141 gttcgttcgg caaactgcct gaagaacgac aacatcgttt atatcggcga cctgatccag
1201 aagaccgaag ccgaaatgct ccgcacgccg aactttggtc gcaagtcgct gaacgaaatc
1261 aaggaagttc tcgcttccat gggtctgcac ctcggcatgg aagtgccggc atggccgcct
1321 gagaacatcg aagatctcgc aaagcgttac gaagaccaat actaacaaac aagaaggcag
1381 accttaaaga ctgcctttcc ccgtcaaaca gcagataagt catctgcatg tgccaggaaa
1441 cggcaggcct taaagaaggc acctgcgtag aaggagaata gcaatgcgcc acggtaattc
1501 aggccgcaag ctcaatagaa ccgccagcca ccgcaaggca atgtttgcca acatggctgc
1561 ttcgctcatc acccatgagc agatcgtcac caccttccg aaggcgaagg aaatccgtcc
1621 gatcgtcgag cgtctcgtga cgctgggcaa gcgcggcgac ctgcacgctc gtcgtcaggc
1681 gatctcgcag at
```

```
A. tum.   MIQKNWQELIKPNKVEFTSSSRTKATLVAEPLERGFGLTLGNALRRVLLS  50
E. coli   -MQGSVTEFLKPRLVDIEQVSSTHAKVTIEPLERGFGETLGNALRRILLS  49
           .*  . * .**  *.    * * *   .******* *******.***

A. tum.   SLRGAAVTAVQIDGVLHEFSSIPGVREDVTDIVLNIKEIAIKMDGDDSKR 100
E. coli   SMPGCAVTEVEIDGVLHEYSTKEGVQEDILEILLNLKGLAVRVQGKDEVI  99
          *. * *** *.*******.*. **.**. .*.**.* .*... * *

A. tum.   MVVRKQGPGSVTAGDIQTVGDIEILNPDHVICTL.DEGAEIRMEFTVNKG 149
E. coli   LTLNKSGIGPVTAADITHDGDVEIVKPQHVICHLTDENASISMRIKVQRG 149
           . . * * *** ** **.**. * **** * ** * *   *   *

A. tum.   KGYVPAE---RNRAEDAPIGLIPVDSLYSPVKKVSYKVENTREGQVLDYD 196
E. coli   RGYVPASTRIHSEEDERPIGRLLVDACYSPVERIAYNVEAARVEQRTDLD 199
          .*****     .  .. ***. **. ****....* **  *   *  *

A. tum.   KLIMTIETNGSVSGEDAVAFAARILQDQLGVFVNFDEPQKEAEEESVTEL 246
E. coli   KLVIEMETTGTIDPEEAIRRAATILAEQLEAFVDLRDVRQPEVKEEKPE- 248
          **.. .** *.. *.*. **.** .**. ... . * *

A. tum.   AFNPALLKKVDELELSVRSANCLKNDNIVYIGDLIQKTEAEMLRTPNFGR 296
E. coli   -FDPILLRPVDDLELTVRSANCLKAFAIHYIGDLVQRTEVELLKTPNLGK 297
           *.* **. ** .*** *******    * *****.*.** *.*.*** *.

A. tum.   KSLNEIKEVLASMGLHLGMEVPAWPPENIECLAKRYEDQY 336
E. coli   KSLTEIKDVLASRGLSLGMRLENWPPASIADE         329
          *** ***.**** ** *** . *** .* *
```

FIG. 3

AGROBACTERIUM TUMEFACIENS RPOA GENE

This application is a continuation-in-part of provisional application Serial No. 60/129,682 filed on Apr. 16, 1999 and a continuation-in-part of provisional application Serial No. 60/134,206 filed on May 14, 1999, both of which are incorporated herein in their entirety by reference.

This work was supported in part by NSF grant MCB-9722227. The U.S. Government may have certain rights to the present invention.

The present invention relates to nucleic acid molecules and constructs containing these nucleic acid molecules and methods of using these constructs to express heterologous genes in hosts. In particular, the nucleic acid molecules of the present invention comprise a DNA sequence encoding at least a portion of the α subunit of the RNA polymerase (referred to herein as RNAP) obtained from the same genus source from which the heterologous genes were originally isolated. The nucleic acid constructs also can optionally comprise, if required for expression of the heterologous genes, at least one gene encoding a transcriptional regulator, also obtained from the same genus as the source of the heterologous genes.

BACKGROUND OF THE INVENTION

Although many host cell systems are well characterized and utilized to express a number of heterologous genes, there are still many genes that cannot be expressed in such host cell systems, as for example, *Escherichia coli* (*E. coli*). It is believed that the lack of expression in these host cell systems is a result of the promoter sequences of the heterologous genes not being recognized by the host RNAP. The present invention has solved this problem by showing that this block in expression can be overcome by co-expression of at least a portion of the rpoA gene product, the gene that encodes the α subunit of the RNAP, obtained from the same genus as the source of the heterologous gene that is desired to be expressed in the new host cell. The co-expressed α subunit of the RNAP from the same genus as the source of the heterologous gene combines with the other subunits of the RNAP, β, β', and σ, to form a functional RNAP. Additionally, if transcriptional regulators, such as transcriptional activators or transcriptional repressors, or additional other subunits of the RNAP, such as β, β' or σ, are required to obtain expression of the heterologous gene, then these additional components also are obtained from the same genus as the source of the heterologous gene. Since two different rpoA genes are present in a single host cell, there will be various combinations of RNAPs present in the host cell (1) RNAP containing two α subunits of the same genus as the host (2) RNAP containing two α subunits from the same genus source as the heterologous gene, and (3) RNAP containing one α subunit from the same genus as the host and one α subunit from the same genus source as the heterologous gene. A heterologous gene is intended to mean a gene that is not from the same source as the host cell.

*Agrobacterium tumefaciens* is a Gram-negative soil bacterium which is the causative agent of Crown Gall disease, affecting primarily dicotyledonous plant species (reviewed in 18, 62). The pathogen incites production of the characteristic tumor through the transfer of a piece of DNA (T-DNA) from the Ti (Tumor inducing) plasmid into susceptible plant cells, with subsequent integration into the host genome. The T-DNA contains genes that direct the biosynthesis of auxin and cytokinin in infected cells (1, 57), resulting in uncontrolled cell division leading to production of the characteristic tumor. The T-DNA also contains genes for the biosynthesis of unique compounds called opines which the bacterium can utilize as a carbon and nitrogen source (39).

Successful transfer of the T-DNA is dependent on the coordinated expression of virulence (vir) genes located on the Ti plasmid but separate from the T-DNA. Expression of vir genes occurs in response to certain phenolic compounds released from wounded plants (54). This expression is augmented by monosaccharides (5, 52), and an acidic pH (38) which are characteristics of plant wound sites. Expression of vir genes requires virA and virG, which are members of the family of two component regulatory systems (60). VirA is an inner membrane associated histidine protein kinase which autophosphorylates in response to the environmental signals (19, 28). The phosphate moiety is subsequently transferred to the aspartate residue of VirG, which in turn activates transcription from promoters containing a specific 12 base pair sequence called the vir box, present in the promoters of all vir genes (29, 44). In addition to virA and virG, other chromosomally encoded genes have been identified in *A. tumefaciens* that have been shown to modulate virulence gene expression either directly or indirectly (12, 15, 20, 61).

The use of *E. coil* as a heterologous host in which to study the regulation of *A. tumefaciens* virulence genes and the mechanism of T-DNA transfer constitutes an ideal model system given the degree of characterization at both the biochemical and genetic level. However, all previous attempts to reconstitute vir gene expression in *E. coil* have not been successful. Possible explanations for the lack of vir gene expression include the presence of unidentified regulatory genes in *A. tumefaciens* required for vir induction, and/or that *E. coli* may contain specific repressor(s) of vir gene induction.

A characteristic of vir gene promoters is the absence of a strong −35 sequence (10). Dnase I footprinting studies have shown that VirG protects a region extending into where the −35 consensus sequence should be (29, 44). It has been suggested that binding of VirG may functionally replace the −35 consensus sequence allowing transcription to occur. This situation is similar to Class II CAP-dependent promoters, in which the CAP binding site overlaps with the −35 sequence. Studies have demonstrated that transcription at Class II CAP-dependent promoters requires interaction between CAP and the α subunit (rpoA) of RNAP (42, 49, 64). Many transcriptional factors from *E. coli* are known to require interaction with the α subunit of RNAP, including FNR (59), GaiR (9), MarA (24), Mer R (7), MetR (23) OxyR (56), OmpR (21), Rob (26), SoxS (25), and TyrR (34). Analysis of the α subunit from *E. coli* indicates the presence of two independent domains, the N-terminal domain and the C-terminal domain (21, 27, 63). The N-terminal domain (NTD) is involved in the assembly of the core polymerase, while the C-terminal domain (CTD) is involved in interaction with certain transcriptional regulators (7, 9, 21, 23, 24, 25, 26, 32, 34, 47, 56, 59). Recently, interaction between the NTD and CAP at Class II CAP-dependent promoters has been demonstrated (42,49).

The present methods of expressing heterologous genes are particularly useful to express multiple genes or operons in a metabolic pathway by co-expressing the rpoA gene product obtained from the same natural hosts from which the genes or operons were originally isolated with the multiple genes. The present method provides an advantage over existing multiple gene expression systems by eliminating the need to separately isolate each gene in the metabolic pathyway and link each gene to a promoter that is functional in the host. Expression of heterologous genes for an entire metabolic pathway in hosts is particularly useful to produce particular metabolites, such as pharmaceuticals, food supplements, chemical products or fine chemical products.

The present invention further provides nucleic acid molecules and methods whereby heterologous genes encoding metabolites in an entire metabolic pathway can be introduced into hosts so that these hosts possess specific catabolic and/or metabolic characteristics that allow the hosts to grow or express gene products under specific environmental conditions. These hosts are useful in bioremediation, bioassays and biocontrol studies where manipulation of natural or symbiotic bacterial flora is desired, such as in the control of parasites or insects where bacterial symbiants are involved.

The present invention broadly relates to the expression of heterologous genes in a host using nucleic acid molecules comprising a gene encoding the complete $\alpha$ subunit of the RNAP obtained from the same genus as the source of the heterologous genes or at least a portion of the $\alpha$ subunit of the RNAP. The host and the heterologous genes to be expressed may be prokaryotic or eukaryotic in origin, however, prokaryotic hosts are preferred. The present invention also relates to a hybrid nucleic acid molecule encoding a hybrid $\alpha$ subunit of RNAP, where a first nucleic acid comprises at least a portion of the rpoA gene encoding the $\alpha$ subunit of an RNAP obtained from the same genus as the source of the host cell and a second nucleic acid comprises at least a portion of the $\alpha$ subunit of an RNAP obtained from the same genus as the heterologous gene.

The present invention specifically discloses the rpoA gene from Agrobacterium encoding the $\alpha$ subunit of the RNAP and the corresponding amino acid sequence. Portions of both the rpoA gene and the $\alpha$ subunit of RNAP of Agrobacterium also are encompassed by the present invention, particularly the sequences disclosed in FIGS. 2A (SEQ ID NO:1) and 2B (SEQ ID NO:2). The rpoA gene is useful in methods of expressing Agrobacterium genes in hosts, particularly prokaryotic host cells. Prior to the present invention, it was not possible to express Agrobacterium genes, particularly Agrobacterium virulence genes, in *E. coli*. Therefore, the present invention provides a method for studying Agrobacterium genes and their regulation.

The invention also relates to genes encoding hybrid rpoA genes that comprise at least a portion of an rpoA gene from the same genus as a heterologous gene which is expressed, such as the Agrobacterium rpoA gene, with the remainder of the rpoA gene obtained from the same genus as the host cell in which the heterologous gene is expressed.

SUMMARY OF THE INVENTION

The present invention is directed to an isolated nucleic acid molecule encoding the complete $\alpha$ subunit of an RNAP of Agrobacterium or at least a portion thereof. Specifically, the present invention is directed to an isolated nucleic acid molecule encoding the complete $\alpha$ subunit of an RNAP of Agrobacterium, in which the amino acid sequence of the $\alpha$ subunit is depicted in. FIG. 2A (SEQ ID NO:1) or at least a portion of this sequence. More specifically, the present invention is directed to an isolated nucleic acid molecule comprising the complete nucleic acid sequence as depicted in FIG. 2B (SEQ ID NO:2) or at least a portion thereof. These isolated nucleic acid molecules encoding at least a portion of the $\alpha$ subunit of an RNAP of Agrobacterium also are optionally linked to a promoter that is functional in the host in which these molecules are expressed. Further, the present invention is directed to vectors containing these nucleic acid sequences or molecules. The vectors are useful in transforming host cells for the expression of heterologous gene(s). The invention is also directed to host cells that are transformed with the nucleic acid molecules described herein. The nucleic acid molecules useful to transform the host cells are operably linked to a promoter and encode an $\alpha$ subunit of an RNAP or at least one heterologous protein.

The present invention is also directed to a hybrid nucleic acid molecule for the expression of at least one heterologous gene in a host cell comprising a first nucleic acid sequence encoding at least a portion of the $\alpha$ subunit of an RNAP obtained from the same genus as the host cell and a second nucleic acid sequence encoding at least a portion of the $\alpha$ subunit of an RNAP obtained from the same genus as the source of the heterologous gene; and vectors containing the hybrid nucleic acid molecule.

The present invention is further directed to a method of expressing at least one heterologous gene in a host cell comprising transforming a host cell with a vector comprising a nucleic acid molecule encoding a complete $\alpha$ subunit of RNAP from the same genus as the source of the heterologous gene or at least a portion thereof, and also transforming the host cell with a vector comprising at least one heterolgous gene. The nucleic acid molecule and the heterologous gene(s) also may be contained in one vector but preferably these sequences are contained within two or more vectors. In a further embodiment, the present invention is also directed to a method of expressing at least one heterologous gene in a host cell comprising transforming a host cell with a vector comprising a hybrid nucleic acid molecule comprising a first nucleic acid sequence encoding at least a portion of the $\alpha$ subunit of an RNAP obtained from the same genus as the host cell and a second nucleic acid sequence encoding at least a portion of the $\alpha$ subunit of an RNAP obtained from the same genus as the source of the heterologous gene, and transforming the host cell with a vector comprising at least one heterologous gene; and culturing the transformed host cell under conditions where the heterologous gene is expressed in the host cell. The host cell also may be transformed with a single vector containing the nucleic acid molecule encoding the complete $\alpha$ subunit of the RNAP, a portion thereof or a hybrid molecule comprising a portion of the $\alpha$ subunit of the RNAP, and with the heterolgous gene(s) or $\alpha$ subunit of the RNAP peferably, two or more vectors may be used. The nucleic acid molecules encoding the $\alpha$ subunit and the heterologous gene(s) may be in separate vectors for transformation of the host cell. The host cell can optionally be transformed with at least one gene encoding a heterologous transcriptional regulator obtained from the same genus as the source of the heterologous gene. The heterologous gene may comprise multiple genes or operons in the same metabolic pathway.

BRIEF DESCRIPTION OF THE DRAWINGS

FIG. 2A. (SEQ ID NO:1) The amino acid sequence of the *A. tumefaciens* $\alpha$ subunit of the RNAP is depicted.

FIG. 2B. (SEQ ID NO:2) The *A. tumefaciens* rpoA gene encoding the *A. tumefaciens* $\alpha$ subunit of the RNAP is depicted. The actual coding sequence for the $\alpha$ subunit is located between nucleotide 355 (atg) and nucleotide 1356 (taa).

FIG. 3. Amino acid sequence alignment of the *A. tumefaciens* and *E. coli* rpoA gene products (SEQ ID NOS: 1 and 3, respectively). Identical amino acid residues at a given position are marked by an asterisk, and conserved substitutions are marked by a dot. Gaps introduced to allow optimal alignment are designated by a dash. The bolded nucleotides show three highly conserved regions between the two amino acid sequences.

FIG. 4A—SDS-PAGE analysis of reconstituted RNAP containing *E. coli* $\beta$, $\beta'$, $\sigma^{70}$ subunits and His-RpoA from *E. coli* or *A. tumefaciens* and stained with Coomassie brilliant blueB.

DETAILED DESCRIPTION OF THE PREFERRED EMBODIMENT

Figure 1:
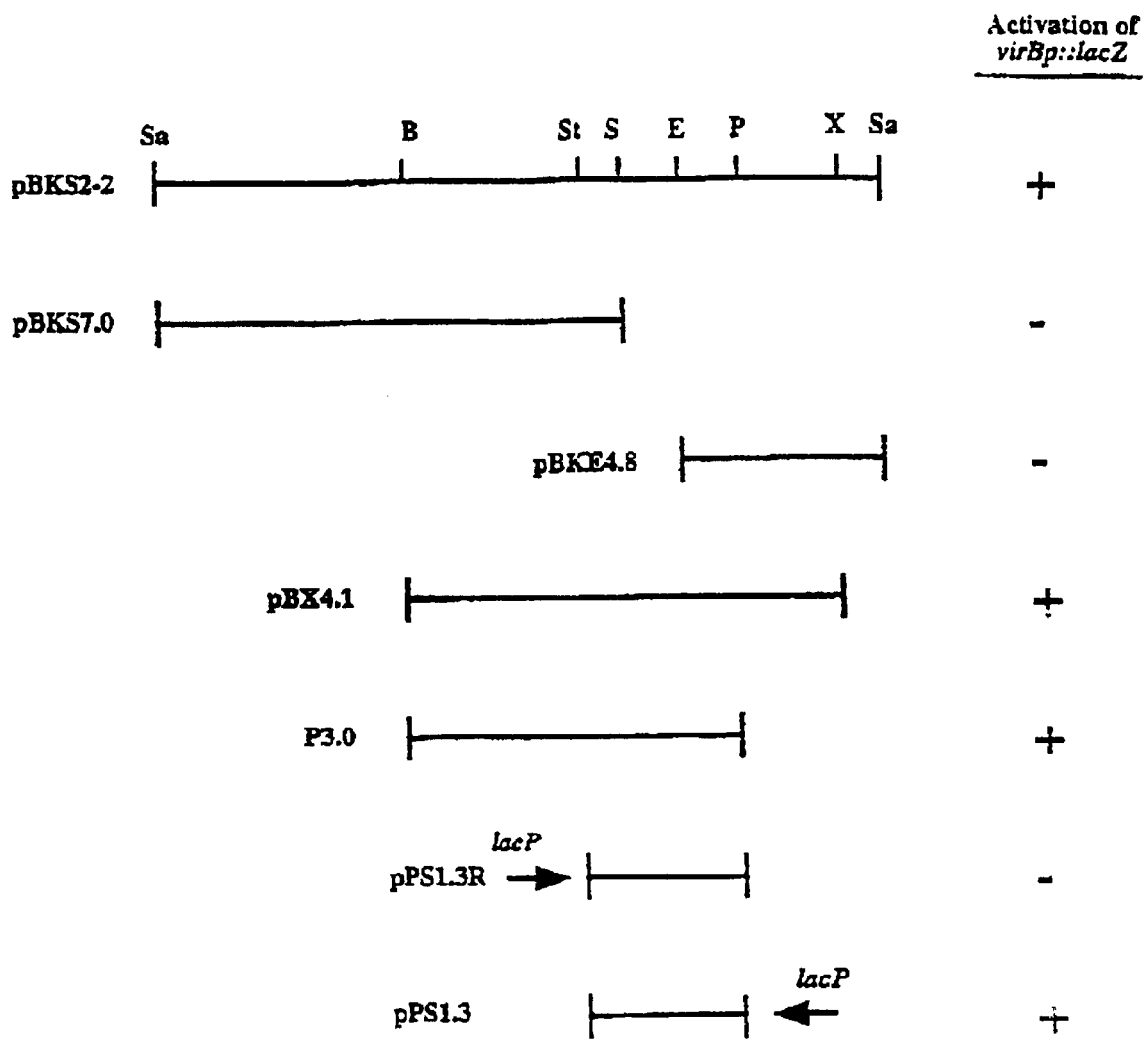
FIG. 1. Physical and genetic map of recombinant plasmids carrying the rpoA gene from *A. tumefaciens* is depicted. Abbreviations: B, BamHI; E. FcoRI; P, PstI; Sa, Sm3A; St, Sttd, X, XhoI Location and direction of rpoA and lac promoter for constructs pPS1.3R and pPS1.3 are indicated by arrows.

Although many well characterized host cells, such as *E. coli*, provide advantages as an expression host cell, it has not been possible to express the genes of many bacteria in these host cells because the promoter sequences of the heterologous genes are not recognized by the host cell RNAP. The present invention provides a method of overcoming this block to expression by co-expressing the α subunit of the RNAP from the same genus as the source of the heterologous genes that are to be expressed in the host, and optionally co-expressing the transcriptional activator from the same genus as the source of the heterologous genes. The success of this method has been demonstrated by showing the expression of the *Agrobacterium tumefaciens* virulence (vir) gene operons in *E. coli*. In this specific example, expression of these genes was shown to require not only the vir gene specific transcriptional regulator but also the rpoA gene from *A. tumefaciens*. The *A. tumefaciens* α subunit of the RNAP is able to assemble with the other subunits (β, β' and σ subunits) of the *E. coli* RNAP to form a functional polymerase which specifically recognizes the Agrobacterium genes in the presence of the Agrobacterium transcriptional regulator, specifically an activator. The results show that this interaction is genus specific, in that, the transcriptional activator from Agrobacterium can only efficiently interact with the rpoA gene product from Agrobacterium and not with that of *E. coli*.

Conventional understanding of gene expression in prokaryotes emphasizes the importance of the transcriptional regulator, either an activator or a repressor. A transcriptional activator is a protein that is needed to turn on the expression of target genes either directly or indirectly whereas repressors are proteins that inhibit the transcription of target genes either directly or indirectly. In the present invention, it is shown that the α subunit of the RNAP is the most critical factor in activating bacterial genes, especially those requiring transcriptional regulators. For example, to express heterologous genes or operons from organism A in organism B, at least a portion of the rpoA gene from organism A is also needed to be co-expressed in organism B. Likewise if transcriptional regulators are required for expression of heterologous genes, the genes encoding the transcriptional regulator(s) from organism A should also be used to transform the host because these regulators can most efficiently interact with RpoA from the same organism A but not as well or at all with that of organism B.

The present method is particularly advantageous when it is used to express particular heterologous metabolic pathway genes in hosts for bioremediation/biocontrol purposes or production of particular metabolites. This approach becomes much more practical than fusing each gene or operon under the control of a known promoter that is functional in the host.

Expression of genes for an entire metabolic pathway in heterologous hosts is useful to produce particular metabolites or to confer to the host specific catabolic or metabolic characteristics that now enables the host to grow or express gene products under specific environmental conditions.

An example of the utility of the present method is shown by the production of a plant growth promoting molecule, indole-3-acetic acid, from *Azospirillum brasilense*, that requires at least 3 biosynthetic genes. *A. brasilense* also possesses multiple genes that encode products that fix nitrogen (65). The multiple genes responsible for encoding these products and the rpoA gene are introduced via one or more vehicles, such as plasmids or cosmids, into a host that is applied to a plant and that expresses the products of the multiple genes. The expressed plant growth promoting molecules and nitrogen fixing molecules affect the growth of the treated plant.

Further Rhizobium, Bradyrhizobium, Azorhiobium and Sinorhizobium are other examples of nitrogen-fixing bacteria, each involving at least two dozen genes for nodulation (symbiosis) and multiple genes for nitrogen fixation. These bacteria, as well as other bacteria that produce useful products for plants, may also be the source of the heterologous genes and the rpoA gene.

The present invention can also be utilized to express gene product(s) in a catabolic pathway that degrades or breaks down toxic or environmentally hazardous products. For example, a Pseudomonas species strain ADP expresses at least four genes that are involved in the degradation of a herbicide, Atrazine (66). These genes are introduced and expressed in a host by applying the host to areas where this herbicide is present, resulting in the degradation of the herbicide on site.

Further, the present invention is useful in providing a biocontrol system that includes a host that expresses heterologous gene products, that for example, kill disease producing organisms on a plant, animal, human or a surface that will support growth of the host. *Pseudomonas chloroaphis* strain 30–84 expresses at least three antifungal metabolites, phenazine-1-carboxylate, 2-hydroxyphenazine-1-carboxlylic acid and 2-hydroxyphenazine that involves four biosynthetic genes and 2 regulatory genes (67). These genes may be introduced into a plant bacteria, such as Rhizobium, that can be applied to a plant to control the growth of fungi on the plant.

The present invention also is useful as an *A. tumefaciens* gene delivery system in heterologous hosts for potential gene delivery or gene therapy systems of *A. tumefaciens* genes to various hosts.

The present invention also can be used to express heterologous genes in *A. tumefaciens* to alter its characteristics (e.g. host specificity) for a broader application of the *A. tumefaciens* mediated gene delivery system.

The present invention also is useful to prepare host cells containing an rpoA gene that is heterologous to the host cell, such as Escherichia. This host cell is useful for studying changes in gene expression patterns in this cell.

The present invention can additionally be used to express particular sets of heterologous genes, including multigene operons/stimulons or genes encoding multi-subunit protein complexes, such as proteosomes or gene libraries in hosts as targets for drug screening and/or diagnostics.

The present invention discloses an isolated nucleic acid molecule encoding the complete α subunit of an RNAP of Agrobacterium or at least a portion thereof. More specifically, an isolated nucleic acid molecule encoding the complete α subunit of an RNAP of Agrobacterium, where the amino acid sequence of the α subunit is depicted in FIG. 2A (SEQ ID NO:1) is disclosed or at least a portion thereof. The portion can be a length of amino acid sequences that is sufficient to express any heterologous gene in the host cell into which it is introduced. The portion of the α subunit of the RNAP also should be of a sufficient length to provide at least one of the following functions: 1) bind to DNA in the promoter region 2) interacts with the other subunits of RNAP; i.e., β, β' and σ to form a functional RNAP, and 3) interacts with the transcriptional activator. More specifically, an isolated nucleic acid molecule comprising at least a portion of the nucleic acid sequence as depicted in FIG. 2B (SEQ ID NO:2) and that encodes at least a portion of the amino acid sequence of FIG. 2A (SEQ ID NO:1) is disclosed. The nucleic acid molecule (rpoA) encoding the Agrobacterium α subunit of the RNAP or a portion of the nucleic acid molecule is useful in the expression of Agrobacterium genes in any prokaryotic host cells.

The present invention is also directed to a nucleic acid molecule encoding a hybrid α subunit of RNAP where the isolated nucleic acid molecule is inserted in a vector and is useful in expressing at least one heterologous gene in a host cell comprising a first nucleic acid sequence encoding at least a portion of the α subunit of an RNAP obtained from the same genus as the host cell and a second nucleic acid sequence encoding at least a portion of the α subunit of an RNAP obtained from the same genus as the source of the heterologous gene. This isolated nucleic acid molecule is operably linked to a promoter so that it is under the control of a promoter that is functional in the host cell. For example, the *E. coli* lac or trp promoters are useful to express the rpoA gene in an *E. coli* host cell. Promoters that function in numerous host cells are well known to persons skilled in the art and can be selected based upon the host cell selected. The second nucleic acid sequence is obtained from any eukaryotic or prokaryotic host cell, and more particularly from a prokaryotic cell, including Gram-negative bacteria, Gram-positive bacteria, acid-fast bacteria, mycoplasma, aerobic bacteria, anaerobic bacteria, and facultative bacteria. More specifically, the bacteria are selected from the genus Agrobacterium, Mycobacterium, Chlamydia, Pseudomonas or Streptomyces. More preferably, it is obtained from Agrobacterium, and most preferably the second nucleic acid sequence encodes the complete amino acid sequence as depicted in FIG. 2A (SEQ ID NO:1) or a portion thereof, with the sufficient length of this portion discussed above. The portion of the of the rpoA gene can be from any position in the gene; i.e., that is from the 5' or the 3' end of the gene, which encodes the N-terminus and C-terminus of the α-subunit, respectively. Most preferably, the nucleic acid molecule portion encodes at least amino acid residues 157 to 336 as depicted in FIG. 2A (SEQ ID NO:1). The nucleic acid molecule can encode as few as 8 consecutive amino acid residues of any portion of FIG. 2A (SEQ ID NO:1). Specifically, a portion comprising at least the amino acid residues 157 to 336, or of less than amino acid residues of 157 to 336, and more specifically amino acid residues 329 to 336 are useful in the present invention. The first nucleic acid sequence is obtained from any bacteria but more preferably from the genus Escherichia, Pseudomonas, Bacillus, Lactobacillus, Clostridium or Rhizobium.

The present invention is directed to a method of expressing at least one heterologous gene in a host cell comprising transforming a host cell with a nucleic acid construct comprising a first nucleic acid sequence encoding at least a portion of the α subunit of an RNAP obtained from the same genus as the source of the host cell, and a second nucleic acid sequence encoding at least a portion of the α subunit of an RNAP obtained from the same genus as the source of the heterologous gene; and with at least one heterologous gene; and culturing the transformed host cell under conditions wherein the heterologous gene is expressed in the host cell. The method further comprising transforming the host cell with at least one gene encoding a heterologous transcriptional regulator obtained from the same genus as the source of the heterologous gene. The heterologous gene may comprise multiple genes or operons in the same metabolic pathway that catalyze the production of a product.

The host cells useful in the present method are prokaryotic cells or eukaryotic cells. Preferably, the host cell is selected from a prokaryotic cell selected from the group consisting of Gram-negative bacteria, Gram-positive bacteria, aerobic bacteria, acid-fast bacteria, mycoplasma, anaerobic bacteria, and facultative bacteria. Preferably, the host cell is obtained from the genus Escherichia, Pseudomonas, Bacillus, Lactobacillus, Clostridium or Rhizobium. Eukaryotic cells may be selected from known mammalian cells that can be grown in cell culture, such as CHO, BHK, COS.

The present invention also is directed to a method of expressing at least one heterologous gene in a host cell comprising transforming the host cell with a vector comprising a nucleic acid molecule encoding a complete α subunit of an RNA polymerase obtained from the same genus as the heterologous gene or a portion of the α subunit of the RNA polymerase, and also transforming the host cell with at least one vector comprising at least one heterologous gene; and then culturing the transformed host cell under conditions where at least one of the beterologous genes is expressed in the host cell. The method further comprises transforming the host cell with at least one gene encoding a heterologous transcriptional regulator obtained from the same genus as the source of the heterologous gene. The transcirptional regulator is a transcriptional activator that interacts with the α subunit of the RNAP to enhance the expression of the heterologous gene. The heterologous gene may comprise multiple genes or operons in the same metabolic pathway.

Preferably, the host cell is transformed with two vectors, one containing the rpoA gene or a portion thereof and one containing at least one heterologous gene. However, the host cell may be transformed with a single vector containing the rpoA and heterologous genes, but more than two vectors can be used to introduce the genes into the host cell depending on the number of genes and the size of the nucleic acid to be introduced.

The host cell may be a prokaryotic cell or a eukaryotic cell. Preferably the host cell is a prokaryotic cell selected from the group consisting of Gram-negative bacteria, Gram-positive bacteria, acid-fast bacteria, mycoplasma, aerobic bacteria, anaerobic bacteria, and facultative bacteria. More preferably the host cell is from the genus Escherichia, Pseudomonas, Bacillus, Lacrobacillus, Clostridium or Rhizobium. Most preferably the host cell is and Escherichia.

The method is useful for the expression of at least one heterologous gene, where the genus of the source of the heterolgous gene is a prokaryotic cell selected from the group consisting of Gram-negative bacteria, Gram-positive bacteria, aerobic bacteria, anaerobic bacteria, and facultative bacteria. More preferably the genus of the source of the heterologous gene is Agrobacterium, Mycobacterium, Chlamydia, Pseudomonas or Streptomyces, and most preferably, the genus is obtained from Agrobacterium.

The method utilizes a nucleic acid molecule that encodes the α subunit of the RNAP the amino acid sequence as depicted in FIG. 2A (SEQ ID NO:1) or at least a portion of the amino acid sequence depicted in FIG. 2A (SEQ ID NO:1). The portion of the amino acid sequence useful in the present method may be from the N-terminus or C-terminus of the α subunit of the RNAP but preferably comprises at least amino acid residues 157 to 336 of the amino acid sequence depicted in FIG. 2A (SEQ ID NO:1) or the portion of the amino acid sequence may comprise less than amino acid residues 157 to 336 of the amino acid sequence depicted in FIG. 2A (SEQ ID NO:1). The portion of the amino acid sequence should comprises at least 8 consecutive amino acid residues of FIG. 2A (SEQ ID NO:1). More specifically, the portion of the amino acid sequence as depicted in FIG. 2A (SEQ ID NO:1) comprises amino acid residues 329 to 336.

The present invention also encompases a purified α subunit of an RNAP of Agrobacterium. More specifically, the purified α subunit of an RNAP of Agrobacterium of the present invention is the amino acid sequence depicted in FIG. 2A (SEQ ID NO:1). The invention is also intended to encompass portions of the purified α subunit of an RNAP disclosed in FIG. 2A (SEQ ID NO:1). More specifically, the purified α subunit of an RNA polymerase of Agrobacterium or a portion thereof is encoded by the nucleic acid is depicted in FIG. 2B (SEQ ID NO:2) or a portion thereof.

A rpoA gene from the same genus as the source of a heterologous gene encoding the α subunit from this source is obtained by methods well known to persons skilled in the art. For example, this gene can be obtained: (1) by complementation of the a temperature sensitive rpoA mutant strain of a known organism, i.e. *E.coli* as discussed below in the preferred embodiment; (2) by Southern hybridization based on DNA sequence homology; (3) by Western blot based on cross reactivity of an antibody against a known RNAP α subunit; and (4) by PCR amplification based on conserved DNA sequences among known rpoA genes. For their expression, the rpoA genes are fused behind or operably linked to a promoter that is known to be operable in the host. The fusion is either a transcriptional fusion or translational fusion. Many standard methods are well known to persons skilled in the art and can be utilized to carryout these methods (See reference 68 which is herein incorporated in its entirety by reference.)

The following specific examples set forth below serve to further illustrate the present invention in its preferred embodiments, and are not intended to limit the present invention to these examples.

EXAMPLES

Bacterial Strains, Plasmids and Media

All strains and plasmids used or constructed are listed in Table 1. Bacterial strains were grown in either LB medium (40), Mannitol Glutamate Luria salts (MG/L) medium (58), or Induction medium containing 1% glucose (61) at 28° C. Induction medium was used for attempts to reconstitute wild type vir gene induction, while MG/L and LB medium were utilized for strains containing virG$^{con}$ (i.e. pSY215 and pLG2). When appropriate, media was supplemented with ampicillin (100 μg/ml), gentamycin (20 μg/ml), kanamycin (50 μg/ml) and tetracycline (20 μg/ml) for *E. coli* and carbenicillin (100 μg/ml), gentamycin (100 μg/ml), kanamycin (100 μg/ml) and tetracycline (5 μg/ml) for *A. tumefaciens*. For determinations of β-galactosidase activity, 5-bromo-4-chloro-3-indoly-β-D-galactopyranoside (X-Gal) and isopropylthio-β-galactoside (IPIG) were included at a final concentration of 75 μg/ml and 1 mM, respectively. Acetosyringone (Sigma) and glucose was included, when necessary at 200 μM and 1%, respectively. For induction assays, *E. coli* stain MC4100 containing constructs indicated in Table 1 were grown to stationary phase in 5 ml of appropriate medium, containing antibiotics as required. These overnight cultures were used to inoculate 125 ml flasks containing 30 ml of identical medium using 0.5 ml as an inoculum. The cultures were incubated at 28° C. with shaking for 16 hours and assayed for β-galactosidase activity according to the method of Miller (40). For reconstitution of virulence gene expression in *E. coli*, plasmid constructs pSY2O4, pLG2, pGP159 and pSL107 were introduced into MC4100 by electroporation. Construct pH098 containing lac-driven *A. turnefaciens* rpoA was then introduced into these strains and initially screened on LB medium (pSY2O4 and pLG2) or induction medium (pGP159 and pSL1O7) containing appropriate antibiotics, 1 mM IPTG, 75 mg/ml X-Gal and 200 μM acetosyringone. Induction assays for these strains were carried out as described above.

Isolation and Subcloning of rpoA Locus

A cosmid clone library of *A. tumefaciens* strain A136, a derivative of strain C58 lacking the Ti plasmid, in pVK102 was described previously (8). The cosmid clones were transformed into *E. coli* strain MC4100 containing plasmid pSY215. Transformants were initially screened for the development of a blue color on induction media containing X-Gal, indicating expression of the virBp::lacZ fusion. A cosmid clone, designated pBK2, was isolated by this procedure and was used for subsequent subcloning attempts, as outlined in FIG. 1.

DNA sequencing was performed by PCR mediated Taq DyeDeoxy Terminator Cycle sequence on an Applied Biosystems model 377 DNA sequencer. The GCG sequence analysis software package (Genetics Computer Group, Madison, Wis.) and the BLAST software package (2) were used for all DNA and protein sequence analysis. The complete nucleotide sequence of the 1.3 Kb PstI-StuI DNA fragment of pPS1.3 was determined on both strands. The rpoA sequence has been deposited into GenBank (accession # AF111855)

Overexpression and Purification of Proteins

For overproduction of the RpoA proteins, rpoA genes from *E. coli* and *A. tumefaciens* were PCR amplified from the MC4100 chromosome and plasmid pBX4.1 (FIG. 1), respectively, using primers designed to contain a BamHI restriction site. [*E. coli* 1) (SEQ ID NO:4) 5'-CCA AAG AGA GGA TCC AAT GCA GGG-3', 2) (SEQ ID NO:5) 5'-CCT TAA CCT GGG ATC CGG TTA CTC G-3'; *A. tumefaciens* 1) (SEQ ID NO:6) 5'-GGA AGG ATC CAA GAT GAT TCA GAA GA-3', 2) (SEQ ID NO:7) 5'-CCT GGAA TCC TGC AGA TGA CTT ATC TG-3']. The PCR products were initially cloned into PCR2.1TOPO (Invitrogen, Inc.), and then subcloned into pQE vectors (Qiagen) to generate pECH4 and pZL-2, containing N-terminal His-tagged fusions to RpoA of *E. coli* and *A. tumefaciens*, respectively.

The His-tagged RpoA proteins of *A. tumefaciens* and *E. coli* were prepared from *E. coli* strain SG13009 (pREP4) containing pZL-2 or pECH4, respectively. Cells were grown at 37° C. in 500 ml of L-Broth containing selective antibiotics to an $OD_{600}$ of 0.3, and then induced with 1 mM IPTG for 3 hours at 37° C. Cells were harvested, resuspended in 20 ml of binding buffer (20 mM Tris-HCl pH7.9, 500 mM NaCl, 5% Glycerol) and lysed by sonication. The lysates were cleared by low speed centrifugation and loaded on a Fast Flow Chelating Sepharose Column charged with $Ni^{2+}$ (Pharmacia, Inc.). The column was attached to a Waters 650 Advanced Protein Purification System, washed extensively with loading buffer containing 25 mM imidazole, and bound protein eluted with buffer containing 100 mM imidazole. Fractions containing greater than 90% RpoA were precipitated by addition of ammonium sulfate to 75% saturation. The resulting pellet was dissolved in a storage buffer (20 mM Tris pH7.9, 40 mM KCl, 10 mM $MgCl_2$, 1 mM DTT, 50% Glycerol) and stored at 20° C.

Recombinant β β' and $\sigma^{70}$ subunits of *E. coli* RNAP were each purified from overexpression strains as described previously (16, 51). Induction was initiated with 1 mM IPTG at 37° C. for 3 hours and the proteins present in inclusion bodies were then purified according to Tang (55). The constitutively active VirG protein $VirG_{con}$) was purified from *E. coli* as described previously (30).

RNAP holoenzymes were reconstituted from individually purified *E. coli* β β' and $\sigma^{70}$, and either *E. coli* or *A. tumefaciens* RpoA as described (3). The molar ration of α, β and β' in the reconstitution reactions was 1:4:8. After reconstitution and thermoactivation in the presence of $\sigma^{70}$, RNAP preparations were further purified by gel exclusion chromatography on a Superose-6 column (Pharmacia) and ion exchange chromatography on a Resource Q column (Pharmacia). The purified RNAP holoenzymes were concentrated by filtration through a C-100 concentrator (Amicon, Inc.) to ~1 mg/ml, and stored in 50% glycerol storage buffer at −20° C.

In Vitro Transcription Assays

For analysis of abortive initiation, 2 pmol of recombinant RNAP holoenzyme containing either *E. coli* or *A. tumefaciens* RpoA was incubated with 10 pmol of template DNA in 10 μl of transcription buffer (40 mM Tris-HCl pH7.9, 40 mM KCl, 10 mM $MgCl_2$) for 10 minutes at 23° C. in the presence or absence of the $VirG^{con}$ protein (2 pmol). As templates, a 130 bp EconRI-HindIII fragment of plasmid pAA121 containing the ga/P1 promoter (−63 to +44) or a 380 bp PCR product of plasmid pSM243cd (Stachel 1985) containing the virB promoter (−248 to +81) were used (4, 10). Abortive initiation reactions were initiated by addition of 0.5 mM initiating dinucleotide (CpA for ga/P1 promoter and ApU for virB promoter) and 0.5 μM [α-$^{32}$p] UTP (ga/P1) or [α-$^{33}$p] ATP (virB) (3000 Ci/mmol). After 25 incubation at 37° C., reactions were terminated by the addition of an equal volume of urea loading buffer. The reaction products were resolved on urea-PAGE (20% polyacrylamide, 19:1 acrylamide:bis) and visualized by autoradiography.

Mobility Shift Assays

Electrophoretic mobility shift DNA binding assays were carried out using a PCR amplified virB promoter labeled with (α-$^{32}$P] dCTP. PCR reactions included 20 μCi (α-$^{32}$P] dCTP, plasmid pSM243cd as template, Primer 1: (SEQ ID NO:8) 5'-TTC CAC GGT GAC GCA TCG AAT G-3', and Primer 2: (SEQ ID NO:9) 5'-CCC CGA TCT CTT AAA CAT ACC TTA TCT CC-3'. Unincorporated nucleotides were removed using the Wizard™ PCR Preps DNA Purification System kit from Promega. Mobility shift reaction mixtures contained 1600 cpm $^{32}$P-labeled virB promoter, 50 mM KCl, 20 mM Tris-HCl pH 7.0, 10 mM $MgCl_2$, 1 mM DTT, 10% Glycerol and 20 μg/ml Herring sperm DNA. Where indicated, 1.5 μM VirG was added, which was sufficient to saturate all VirG binding sites on the promoter, and His-RpoA was added at 150–500 nM final concentration. Reactions were incubated for 30 minutes at 22° C., loaded onto 6% polyacrtlamide, 10% glycerol vertical slab gels in 0.5×TBE buffer (46) and electrophoresed at 20V/cm at 4° C. for 2 hours. Following electrophoresis the gels were dried and autoradiographed overnight at room temperature.

Identification of an *A. tumefaciens* Gene that is Required for vir Gene Expression in *E. coli*

To reconstitute vir gene induction in *E. coli*, plasmid construct pGP159 containing virA and virG under the control of their native promoters and a lacZ reporter gene fused downstream of the virB promoter (virBp:lacZ fusion) was introduced into *E. coli* strain MC4100. The resulting strain failed to activate transcription of the fusion in response to acetosyringone (AS). The inability of pGP159 to activate transcription may have been due to a lack of expression of the virA/virG genes, which are under the control of their native promoters. To address this possibility, the plasmid pSL107 was utilized, which contains virA and virG under the control of the lac promoter and virBp:lacZ. Introduction of pSL107 into MC4100 also failed to activate expression of the vir gene fusion in the presence of AS and IPTG. The observed lack of expression was not due to a lack at expression of virA and/or virG as both proteins were present at detectable levels by Western blot (data not shown). Since VirA and VirG were present, the VirA/VirG signal transduction mechanism may not be functional in *E. coli*. This possibility was addressed through the use of pSY215 which contains a constitutively active $virG^{con}$ under the control of the lac promoter and vtrBp::lacZ. The $virG^{con}$ is able to activate expression of the virBp::lacZ fusion in *A. tumefaciens* strains independent of virA and acetosyringone (17, 31, 45). When pSY215 was introduced into MC4100, once again no expression of the virBp::lacZ fusion was observed. This suggested that additional genes from *A. tumefaciens* may be required or that *E. coli* may contain specific repressors of vir gene expression.

To determine if additional genes from *A. tumefaciens* were required, a cosmid library constructed from chromosomal DNA of a Ti plasmidless strain A136, was introduced into MC4100(pSY215). Screening of the resulting transformants revealed the presence of a clone which produced a light blue color on colonies grown on induction media containing X-Gal and IPTG. This cosmid clone, designated pBK2, contains a 25 Kb DNA insert. In order to identify the gene residing in pBK2 required for expression of virBp::lacZ, overlapping subclones of pBK2 were generated which were introduced into MC4100(pSY215). Expression of the fusion was detected following introduction of pBX4.1, but not pBKS7.0 or pBKE4.8 (FIG. 1 & Table 2). The inability of pBKS7.0 and pBKE4.8 to activate expression of the fusion indicated that the 0.55 Kb region between these two subclones is required for expression of the fusion. Given this information, a 1.3 Kb StuI-PstI DNA fragment from pBX4.1 was isolated and subcloned it into pTZ18R and pTZ19R yielding pPS1.3R and. PPS1.3, respectively. This resulted in two constructs in which the lac promoter on the vector drives transcription from either end of the fragment. Expression of the vir fusion was detected only with pPS1.3, indicating the absence of promoter elements in the fragment and the responsible gene is in the direction of PstI to SruI. Subclone pPS1.3 resulted in the highest level of expression of the fusion, almost 15 fold higher than pBK2, and 40 fold higher than the vector control. This could be due to both increased copy number of the gene and increased gene expression by the strong lac promoter (Table 2).

Characterization of the Identified Gene

The DNA sequence of the entire 1.3 Kb StuI-PstI fragment was obtained from both strands. Analysis of the DNA sequence revealed an open reading frame of 1,008 base pairs, in the predicted transcriptional direction, sufficient to encode a polypeptide of 336 amino acids as shown in FIG. 2A (SEQ ID NO:1). Nucleotide and protein searches of GenBlank and Swiss-Prot database indicated a high degree of similarity to rpoA genes, encoding the α subunit of RNAP. Comparison with rpoA from *E. coli* indicated 62.15% sequence similarity and 51.4% sequence identity at the amino acid level as shown in FIG. 3. Three highly conserved regions can be identified from the distribution of homologous amino acid residues between *E. coli* and *A. tumefaciens* rpoA homologues. One region extends from residue 30 to 51 near the N-terminus (20 of 22 identical), with the other two present in the C-terminal domain extending from residue 256 to 270 (13 of 15 identical) and from residue 276 to 315 (30 of 42 identical). A notable difference is the presence of an additional eight residues at the C-terminus of the *A. tumefaciens* RpoA, compared to RpoA of *E. coli*. A potential Shine-Dalgamo sequence, GAAGGT, was found extending from −7 to −12 bp upstream of the proposed ATG initiation codon of rpoA. Analysis of partial DNA sequence obtained from pBKS7.0 and pBKE4.8 indicated the presence of regions upstream and downstream of rpoA with a high degree of sequence similarity to rpsK and rplQ, encoding S11 and L17 ribosomal proteins, respectively, possibly forming an operon structure similar to *E. coli*.

Figures 4A, 4B:
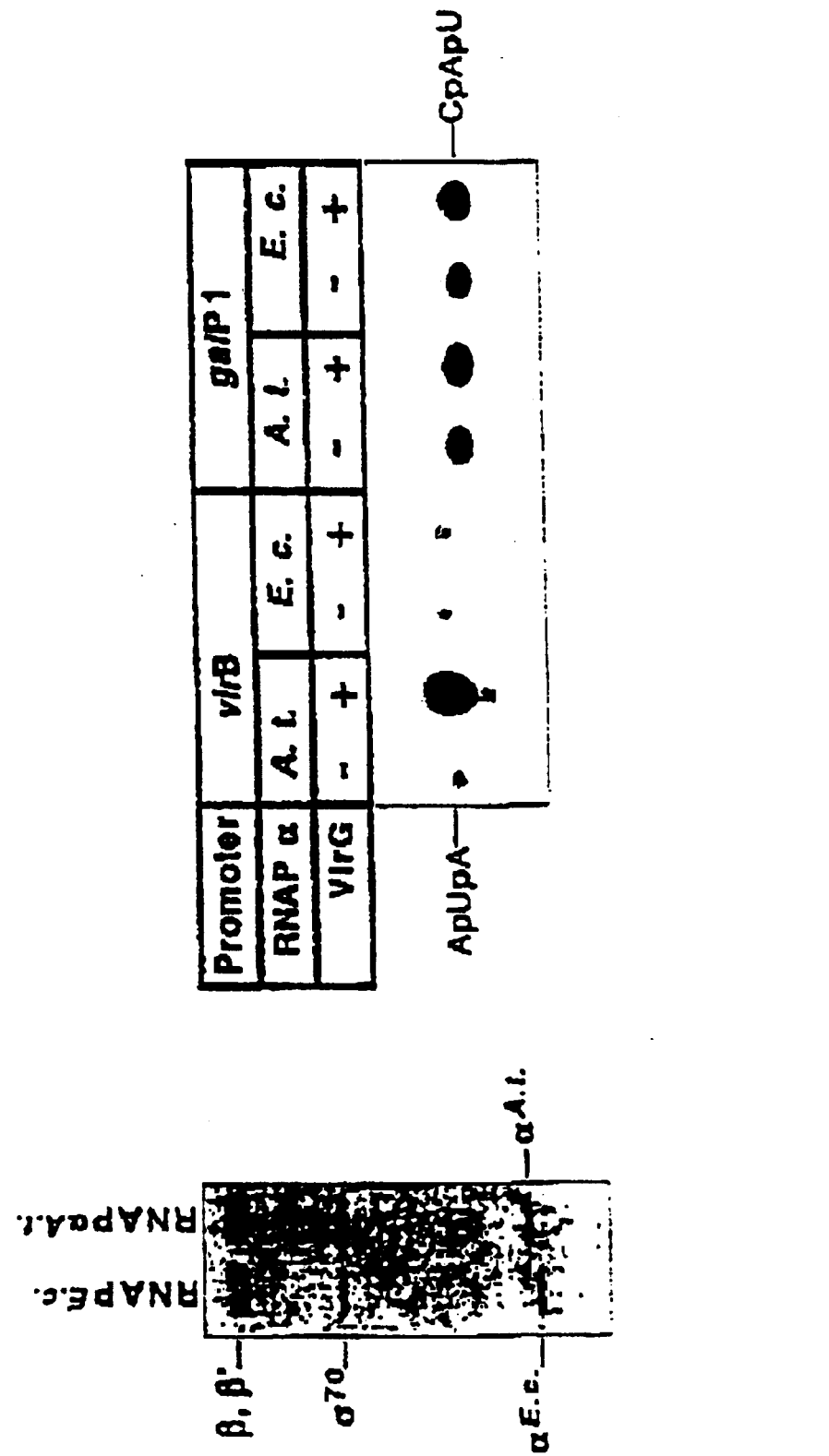
FIGS. 4A and B. Assembly of His-rpoA into RNAP, and in vitro transcription assays.
FIG. 4B—In vitro transcription from virB and galP1 promoters in the absence and presence of VirG$^{con}$. The figure shows the result of a multiround transcription reaction employing reconstituted RNAP containing His-rpoA from either *E. coli* or *A. tumefaciens*. Where indicated, 2 pmol of VirG$^{con}$ was added to the reaction.

Confirmation of the ORF was achieved by construction of a His-tagged rpoA fusion as described above, which yielded a polypeptide of the predicted size (~37 Kd) that is slightly larger than *E. coli* RpoA (FIG. 4A). Furthermore, the DNA clone from *A. tumefaciens* was able to complement a temperature sensitive rpoA mutant of *E. coli*, HN317, proving that it does encode a functional homologue of the RNAP α subunit.

In vitro Transcription of the virB Promoter

In vitro assays involving the rpoA subclones and a constitutive virG$^{con}$, in vitro transcription assays were performed. Purified individual components of *E. coli* RNAP, β β' and σ$^{70}$, were mixed with either His-RpoA of *E. coli* or *A. tumefaciens* and high molecular weight RNAP complexes were purified by sizing column (see Materials and Methods). As shown in FIG. 4A, both RpoA molecules were able to successfully assemble with the *E. Coli* β β' and σ$^{70}$ subunits into complete RNAP holoenzymes. When tested for in vitro transcription, both RNAP holoenzymes were equally efficient in initiating transcription from a α$^{70}$ dependent *E. coli* ga/P1 promoter (FIG. 4B), demonstrating that the hybrid RNAP containing RpoA (α-subunit of RNAP) of *A. tume-faciens* is a functional enzyme. Furthermore, no significant differences were detected in the amount of the transcript produced in the presence or absence of virG$^{con}$. When the virB promoter was used as a template, the *E. coil* KNAP could activate low level transcription but no difference was evident with or without the VirG$^{con}$ protein. In contrast, the hybrid RNAP containing *A. tumefaciens* RpoA was able to activate transcription from the virB promoter at low levels, and addition of the VirG$^{con}$ increased transcription by 4–5 fold as measures by quantification of the gel (FIG. 4B). These results confirm the in vivo assays demonstrating that only RNAP containing RpoA of *A. tumefaiens* is able to efficiently initiate transcription from the virB gene promoter in a VirG$^{con}$ dependent manner. The inability of *E. coli* RNAP to efficiently express the vir fusion even in the presence of the VirG$^{con}$ suggests that *E. coli* RpoA can not make the required contacts with the VirG$^{con}$ protein.

Specific Interaction Between the VirG$^{con}$ and RpoA of *A. tumefaciens*

Figure 5A:
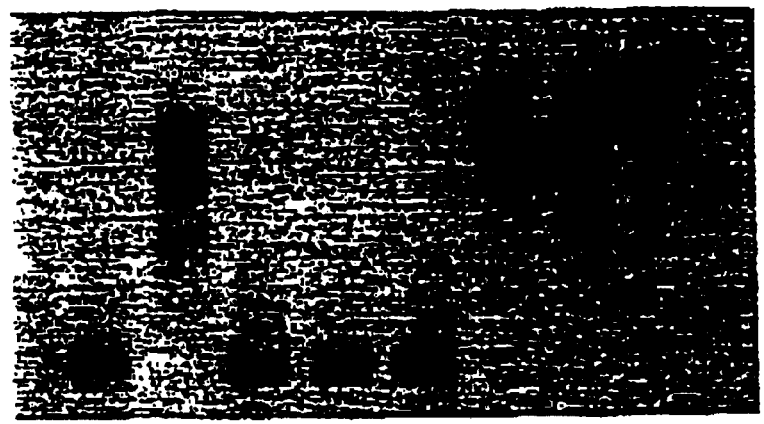
FIG. 5. Protein-protein and protein-DNA interactions between RpoA, VirG$^{con}$ and the virB promoter. The figures show electrophoretic mobility shift assays of [$^{32}$P]-labeled virB promoter containing purified VirG$^{con}$ and His-RpoA from *E. coli* in FIG. 5A or *A. tumefaciens* in FIG. 5B Lane 1: Promoter only, Lane 2: Promoter+VirG$^{con}$, Lane 3: Promoter+150 nM RpoA, Lane 4: Promoter+300 nM RpoA, Lane 5: Promoter+600 nM RpoA, Lane 6: Promoter+VirG$^{con}$+150 nM RpoA, Lane 7: Promoter+VirG$^{con}$+300 nM RpoA, Lane 8: Promoter+VirG$^{con}$+600 nM RpoA.
Figure 5B:

Since the C-terminal domain of the *E. coli* RpoA was known to interact with the A+T rich "UP element of certain promoters (Ross 1993), the *E. coli* and *A. tumefaciens* RpoA proteins were tested to determine if these proteins have different affinities for the virB promoter. As shown in FIG. 5 (lanes 3, 4 and 5), *A. tumefaciens* RpoA was able to shift the mobility of the labeled virB promoter at the highest concentration used (600 nM), whereas the same concentration of *E. coil* RpoA did not, suggesting that the RpoA of *A. tumefaciens* has a higher affinity for the virB promoter than RpoA of *E. coli*. Similar mobility shift assays were carried out to determine if His-RpoA of *E. coli* and *A tumefaciens* interact differently with VirG$^{con}$ at the virB promoter. Increasing amounts of RpoA were used in. combination with a saturating quantity of VirG$^{con}$ for the virB promoter (FIG. 5, lane 2) The concentration of VirG$^{con}$ used was determined through separate mobility shift assays in which increasing amounts of VirG$^{con}$ resulted in two separate shifts in mobility, corresponding to binding of VirG$^{con}$ at the two vir boxes of the virB promoter (data not shown). At the three concentrations of *E. coli* RpoA used, there was no additional shift in the mobility of the promoter VirG$^{con}$ complex (FIG. 5A, lanes 6. 7 and 8). However, when RpoA from *A. tumefaciens* was used, two separate shifts were observed (FIG. 5B, lanes 6, 7 and 8) which suggests specific interactions between VirG$^{con}$ and RpoA from *A. turnefaciens*. These results provide further evidence suggesting that RpoA from *A. turnefaciens* may possess a higher affinity for VirG$^{con}$ compared to RpoA from *E. coli*.

Combination of virA/G and rpoA of *A. tumefaciens* is Insufficient to Reconstitute Acetosyringone Mediated vir Gene Induction in *E. coli*

To determine if the signaling mechanism, resulting in vir gene activation, can be reconstituted in *E. coli*, a wild type virA and virG was used in combination with *A. turnefaciens* rpoA. M04100 harboring two plasmid constructs, one containing a virBp::lacZ fusion as well as wild type virA/virG under their native promoters (pGP159), and the other containing a lac-driven *A. tumefaciens* rpoA gene (pH098), did not show any significant increase in β-galactosidase activity in the presence of acetosyringone (data not shown). The possibility that lack of expression of virA and/or virG may account for this result was again addressed through the use of pSL107 which contains lac-driven virA/virG and virB-p::lacZ. However, it was not possible to obtain significant expression of the fusion in MC4100 harboring pSL107 and pH098. Introduction of pH098 into MC4100(pLG2), containing lac-driven VirG$^{con}$ and virBp::lacZ, however, resulted in a significant increase in β-galactosidase activity, demonstrating that pH098 is able to produce a functional RpoA protein. These results suggest that the signal transduction mechanism of VirA/VirG may not be functional in E. coli.

The present invention discloses that it is possible to obtain the expression of heterologous genes that previously could not have been expressed in a host, such as E. coli, by including a rpoA gene or a portion thereof from the same host genus as the expressed gene is obtained The ability to use E. coli as a heterologous system provides investigators with a valuable tool for studying these various processes. The identification of a chromosomally encoded A. tumefaciens rpoA gene and the demonstration that it constitutes one of the components required for expression of a virBp::lacZ gene fusion in a heterologous E. coli background supports the present invention. The rpoA gene of E. coli has been extensively studied, particularly with regard to interactions with transcriptional regulators, and suggests that interaction between VirG and RpoA may be required for efficient transcription of virulence genes.

The inability of pGP159 or pSL107 to activate transcription of the virBp::lacZ fusion suggested that either signal transduction between VirA and VirG was not functional, or that additional gene(s) were required from A. tumefaciens for activation. The use of pSY215 containing a virG$^{con}$ mutant allowed us to evaluate vir gene expression in a virA-independent manner, eliminating the need for signal transduction. The lack of expression obtained with pSY215 in E. coli, combined with its ability to function in a Ti plasmidless A. tumefaciens strain suggested that additional A. tumefaciens gene(s) were required for expression. The introduction of pPS1.3 containing lac driven rpoA into MC4100(pST215) resulted in a significant increase (40 fold) in transcription of the virBp::lacZ fusion compared to the control vector. Verification that rpoA is required was obtained through the use of subclone pPS1.3R, which did not activate expression of the fusion. This construct is identical to pPS1.3, but the direction of transcription of rpoA is opposite to that of the lac promoter. The observation that A. tumefaciens rpoA was able to complement a temperature sensitive rpoA mutant in E. coli demonstrates an ability to function at essential E. coli promoters. This is evident from the in vitro transcription assay where the hybrid NAP was equally effective as E. coli RNAP in transcribing a $\sigma^{70}$-dependent ga/P1 promoter (FIG. 4B). While the expression of the virBp::lacZ fusion (Table 1) was significantly increased, the level of expression was relatively low in comparison to expression in A. tumefaciens (31). The relatively low expression of the virBp::lacZ fusion may have been a consequence of the presence of RNAP containing RpoA of E. coli. In order to remove possible interference from E. coli RpoA, in vitro transcription assays using reconstituted RNAP holoenzymes containing His-RpoA from either E. coli or A. tumefaciens were carried out. Using purified E. coli β, β' and $\alpha^{70}$ subunits, it was demonstrated that both of the His-RpoA were able to assemble into multi-subunit RNAP holoenzymes (FIG. 4A). The results of the in vitro transcription assays demonstrated that VirG$^{con}$-dependent transcription of the virBp::lacZ fusion requires RNAP containing A. tumefaciens RpoA, although the two reconstituted holoenzymes exhibited essentially identical activity in transcription from the ga/P1 promoter, with no significant difference in the presence or absence of VirG$^{con}$ (FIG. 4B). Another possible explanation for the relatively low induction in E. coli may due to the presence of E. coli sigma factors in the RNAP holoenzymes. It is conceivable that E. coli sigma factors have a lower affinity for the virB promoter than sigma factors from A. turnefaciens. Although the vegetative sigma factor from A. turnefaciens has been identified (50), it is unclear whether this or an alternative sigma factor is involved in vir gene transcription.

Previous reports have identified the presence of an "UP element" in certain E. coli promoters which is required for optimal transcription (14, 41, 47). This element extends from −40 to −60 bp upstream of the transcription start site and is highly A+T rich. Interestingly, the virB promoter contains an A+T rich sequence from −40 to −60 that overlaps wit the VirG binding sites. Whether this region of the promoter constitutes a true "UP element" is unknown. From the gel shift assays, the A. tumefaciens RpoA appears to have a higher affinity for the virB promoter than E. coli RpoA (FIG. 5A and B), although the importance of this observation is unclear at this time. The results of the mobility shift assay suggest that E. coil RpoA is unable to bind to VirG$^{con}$ at the virB promoter. In contrasts, A. tumefaciens RpoA appears to exhibit cooperative binding with two distinct shifts in the mobility of the VirG$^{con}$-virB promoter complex. Taken together, these results indicate that RNAP containing E. coli RpoA may be unable to interact effectively with VirG$^{con}$, and therefore can not activate transcription from the virB promoter. Since the virB promoter contains two binding sites for VirG, the presence of two shifts obtained with increasing amounts of A. tumefaciens RpoA may be a consequence of RpoA interacting with VirG at each vir box.

The two component regulatory system, composed of virA and virG, is indispensible for transcription of virulence genes within A. tumefaciens. However, virA and virG are insufficient to activate transcrition from virulence gene promoters within E. coli cells, indicating a requirement for additional A. tumefaciens gene(s).

In examining vir gene expression in E. coli, attempts to reconstitute wild type virulence gene expression in E. coli were not successful. The use of virA and virG under the control of the lac promoter means that sufficient levels of virA and virG should be present for signal transduction to take place. One possible explanation may be that E. coli is unable to correctly insert virA into the inner membrane. Alternatively, even, though virA may be inserted into the inner membrane correctly, dimerization of virA which is required for activity in. A. turnefuciens (43) may be defective. A more likely explanation may be that additional gene(s) from A. tumefaciens are required for efficient signal transduction. An unresolved question is the exact mechanism of sensing of phenolic inducers by the virA/virG system. The two possible mechanisms involve direct binding of the inducer by virA, or binding by a second receptor which then interacts with virA. Although genetic evidence supporting direct binding of inducers by virA has been reported (36, 37), all attempts to demonstrate direct binding by virA have been unsuccessful. Conversely, there have been reports in which binding of phenolic compounds by proteins other than virA have been detected (13, 35), although there is no evidence to link these proteins with vir gene induction. The search for additional A. tumefaciens gene(s) involved in the signal transduction should be simplified by determining that virG$^{con}$ mediated expression of virulence genes requires RpoA from A. tumefaciens. The present invention provides the basis to examine vir gene expression as well as the T-DNA transfer process in E. coli.

This specific example shows that for the expression of vir genes in E. coli, both rpoA and virG from A. tumefaciens are required for transcriptional activation of a vir promoter in E. coli. It has been determined that the rpoA gene, encoding the α subunit of RNAP, confers significant expression of a virBp;;lacZ fusion in E.coli in the presence of an active transcriptional regulator virG gene. In vitro transcription assays were conducted using either reconstituted E. coli RNAP or hybrid RNAP in which the α subunit was derived from A. tumefaciens. Both RNAPs were equally efficient in transcription from a σ⁷⁰-dependent E. coli galP1 promoter, however, only the hybrid RNAP was able to transcribe the virB promoter in a virG-dependent manner.

Evidence is also presented which indicates that virG interacts with rpoA from A. tumefaciens but not with rpoA from E. coli. This observation suggests that in order for successful transcription of vir genes to occur, specific interaction(s) between the A. tumefaciens α subunit of RNAP and virG is required.

As shown in FIG. 3, one of the major difference between the RpoA sequences of A. tumefaciens and E. coli is the presence of an extra 8 consecutive amino acids at the C-terminus of A. tumefaciens RpoA (amino acids 329 to 336). To test if these C-terminal 8 consecutive amino acids are important in mediating vir gene activation in E.coli, a plasmid construct was generated from pPS1.3 by deleting the DNA coding for the last 8 amino acids using site directed mutagenesis. The resulting plasmid pAD8 encodes 328 amino acid long A. tumefaciens RpoA, lacking the original amino acids from 329 to 336.

The vir gene activating ability of this construct was tested by introducing pAD8 into E.coli strain MC4100 harboring pSY215 which contains virA, virG and virB::lacZ fusion. As negative and positive controls, vector plasmid pQE31 or pPS1.3 which encodes intact RpoA of A. tumefaciens was introduced into MC4100(pSY215), respectively. The vir gene activation was monitored by measuring the β-galactosidase activities. As shown in Table 3, pAD8 failed to activate β-galactosidase activity whereas the pPS1.3 induced a high level β-galactosidase activity. These results indicate that the C-terminal 8 amino acids of A. tumefaciens RpoA are essential for the vir gene activation in E.coli.

These experiments also demonstrate that incorporation of a rpoA gene of a prokaryote, such as A.tumefaciens, into an expression vector will promote the expression of genes from the prokaryotic cells in other prokaryotic cells, such as E. coli. Expression of this expression vector comprising at least a portion of an A. tumefaciens gene is a useful gene delivery system in heterologous hosts for gene delivery and gene therapy. Further, incorporation of at least a portion of an rpoA gene derived from the same cells as one or more heterologous genes, into a vector containing the heterologous genes, provide improved systems for expressing the heterologous genes. These expression vectors which comprise one or more heterologous genes and at least a portion of an rpoA gene derived from the same cells as the heterologous genes, are useful in the production of selected metabolites, by expression genes for an entire metabolic pathway in a heterologous host.

The following list of publications referred to in the specification are herein incorporated in their entirety by reference.

References

1. Akiyoshi, D. E., H. Klee, R. M. Amasino, E. W. Nester and M. P. Gordon. 1984. T-DNA of Agrobacterium tumefaciens encodes an enzyme of cytokinin biosynthesis. Proc. Natl. Acad. Sci. USA. 81:5994–5998.
2. Altschul, S. F., T. L. Madden, A. A. Schaffer, J. Zhang, Z. Zhang, W. Miller and D. J. Lipman. 1997. Gapped BLAST and PSI-BLAST: A new generation of protein database search programs. Nucleic Acids Res. 25:3389–3402.
3. Borukhov, S. and A. Goldfarb. 1993. Recombinant Escherichia coli RNAP: identification of individually overexpressed subunits and in vitro assembly. Protein Expr. Purif. 1993. 4:503–511.
4. Burns, H. D., T. A. Belyaeva, S. J. Busby and S. D. Minchin. 1996. Temperature dependence of open-complex formation at two Escherichia coli promoters with extended −10 sequences Biochem. J. 317:305–311.
5. Cangelosi, G. A., R. G. Ankenbauer and E. W. Nester. 1990. Sugars induce the Agrobacterium virulence genes through a periplasmic binding protein and a transmembrane signal protein. Proc. Natl. Acad. Sci. USA. 87:6708–6712.
6. Casadaban, M. J. 1976. Transposition and fusion of the lac genes to selected promoters in Escherichia coli using bacteriophage lambda and mu. J. Mol. Biol. 104:541–555.
7. Caslake, L. F., S. I. Ashraf and A. O. Summers. 1997. Mutations in the alpha and sigma-70 subunits of RNAP affect expression of the mer operon. J. Bacteriol. 179:1787–1795.
8. Charles, T. C. and E. W. Nester. 1993. A chromosomally encoded two-component sensory transduction system is required for virulence of Agrobacterium tumefaciens. J. Bacteriol. 175:6614–6625.
9. Choy, H. E., S. W. Park, T. Aki, P. Parrack, N. Fujita, A. Ishihama and S. Adhya. 1995. Repression and activation of transcription by Gal and Lac repressors: involvement of alpha subunit of RNAP. EMBO J. 14:4523–4530.
10. Das, A., S. Stachel, P. Ebert, P. Allenza, a. Montoya and E. W. Nester. 1986. Promoters of Agrobacterium tumefaciens Ti plasmid virulence genes. Nucleic Acids Res. 14:1355–1364.
11. Das, A. and G. J. Pazour. 1989. Delineation of the regulatory region sequences of Agrobacterium tumefaciens virB operon. Nucleic Acids Res. 17:4541–4550.
12. D'Sonza-Ault, M. R., M. B. Cooley and C. I. Kado. 1993. Analysis of the Ros repressor of Agrobacterium virC and virD operons: molecular intercommunication between plasmid and chromosomal genes. J. Bacteriol. 175:3486–3490.
13. Dye, F. and F. M. Delmotte. 1997. Purification of a protein from Agrobacterium tumefaciens train A348 that binds phenolic compounds. Biochem. J. 321:319–324.
14. Gaal, T., W. Ross, E. E. Blatter, H. Tang, X. Jia, V. V. Krishnan, N. Assa-Munt, R. H. Ebright and R. L. Gourse. 1996. DNA-binding determinants of the α subunit of RNAP: novel DNA-binding domain architecture. Genes and Dev. 10:16–25.
15. Gray, J., J. Wang and S. B. Gelvin. 1992. Mutation of the miaA gene of Agrobacterium tumefaciens results in reduced vir gene expression. J. Bacteriol. 174:1086–1098.
16. Gribskov. M. and R. R. Burgess. 1983. Overexpression and purification of the sigma subunit of Escherichia coli RNAP. Gene. 109–118.
17. Han, D. C., C. Y. Chen, Y. F. Chen and S. C. Winans. 1992. Altered-function mutations of the transcriptional regulatory gene virG of Agrobacterium tumefaciens. J. Bacteriol. 174:7040–7043.
18. Hooykaas, P. J. J. and A. G. M. Beijersbergen. 1994. The virulence system of Agrobacterium tumefaciens. Ann. Rev. Phytopathol. 32:157–179.
19. Huang, Y., P. Morel, B. Powell and C. I. Kodo. 1990. ViRA, a coregulator Ti-specific virulence genes, is phosphorylated in vitro. J. Bacteriol. 172:1142–1144.
20. Huang, M. L., G. A. Cangelosi, W. Halperin and E. W. Nester. 1990. A chromosomal Agrobacterium tumefaciens gene required for effective plant signal transduction. J. Bacteriol. 172:1814–1822.
21. Igarashi, K. and Ishihama, A. 1991. Biparite functional map of the E. coli RNAP subunit: involvement of the C-terminal region in transcriptional activation by cAMP. Cell 65:1015–1022.
22. Ishihama, A., N. Shimamoto, H. Aiba, K. Kawakami, H. Nashimoto, A. Tsugawa and H. Uchida. 1980.

23. Jaffri, S., M. L. Urbanowski and G. V. Stauffer. 1995. A mutation in the rpoA gene encoding the α subunit of RNAP that affects metE-metR transcription in *Escherichia coli*. J. Bacteriol. 177:524–529.
Temperature-sensitive mutations in the α subunit of *Escherichia coli* RNAP. J. Mol. Biol. 137:137–150.
24. Jair, K. W., R. G. Martin, J. L. Rosier, N. Fujita, A. Ishihma, and R. E. Wolf, Jr. 1995. Purification and regulatory properties of MarA protein, a transcriptional activator of *Escherichia coli* multiple antibiotic and superoxide resistance promoters. J. Bacteriol. 177:7100–7104.
25. Jair, K. W., W. P. Fawceit, N. Fujita, A. Ishihama, and R. E. Wolf, Jr. 1996. Ambidextrous transcriptional activation by SoxS: requirement for the C-terminal domain of the RNAP alpha subunit in a subset of *Escherichia coli* superoxide-inducible genes. Mol. Microbiol. 19:307–317.
26. Jair, K. W., X. Yu, K. Skarstadt, B. Thony, N. Fujita, A. Ishihama and R. E. Wolf, Jr. 1996. Transcriptional activation of promoters of the superoxide and multiple antibiotic resistance regulons by rob, a binding protein of the *Escherichia coli* origin of chromosomal replication. J. Bacteriol. 178:2507–2513.
27. Jeou, Y. H., T. Negishi, M. Shirakawa, T. Yamazaki, N. Fujita, A. Ishihama and Y. Kyogoku. 1995. Solution structure of the activator contact domain of the RNAP α subunit. Science. 270:1495–1497.
28. Jin, S., T. Roitsch, R. Ankenbauer, M. P. Gordon and E. W. Nester. 1990. The VirA protein of *Agrobacterium tumefaciens* is autophosphorylated and is essential for vir gene regulation. J. Bacteriol. 172:525–530.
29. Jin, S., T. Roitsch, P. J. Christie and E. W. Nester. 1990. The regulatory VirG protein specifically binds to a cis-acting regulatory sequence involved in transcriptional activation of Agrobacterium tumefaciens virulence genes. J. Bacteriol. 172:531–537.
30. Jin, S. G., R. K. Prusti, T. Roitsch, R. G. Ankebauer and E. W. Nester. 1990. Phosphorylation of the VirG protein of *Agrobacterium tumefaciens* by the autophosphorylated VirA protein: essential role in biological activity of VirG. J. Bacteriol. 172:4945–4950.
31. Jin, S., Y. N. Song, S. Q. Pan and E. W. Nester. 1993. Characterization of a virG mutation that confers constitutive virulence gene expression in Agrobacterium. Mol. Microbiol. 7:555–562.
32. Kolb, A., K. Igarashi, A. Ishihama, M. Lavigne, M. Buckle and H. Buc. 1993. *E. coli* RNAP, deleted in the C-terminal part of its α subunit, interacts differently with the cAMP-CAP complex at the lacP1 and at the ga/P1 promoter. Nucleic Acids Res. 21:319–326.
33. Knauf, V. C. and E. W. Nester. 1982. Wide host range cloning vectors: a cosmid clone bank of an Agrobacterium Ti plasmid. Plasmid. 8:45–54.
34. Lawley, B., N. Fujita, A. Ishihama and A. J. Pittard. 1995. The TyrR protein of *Escherichia coli* is a class I transcription activator. J. Bacteriol. 177:238–241.
35. Lee, K., M. W. Dudley, K. M. Hess, D. G. Lynn, R. D. Joerger and A. N. Binns. 1992. Mechanism of activation of Agrobacterium virulence genes: identification of phenol-binding proteins. Pro. Natl. Acad. Sci. USA. 89:8666–8670.
36. Lee, Y. W., S. Jin, W. S. Sim and E. W. Nester. 1995. Genetic evidence for direct sensing of phenolic compounds by the VirA protein of *Agrobacterium tumefaciens*. Proc. Natl. Acad. Sci. USA. 92:12245–12249.
37. Lee, Y. W., S. Jin, W. S. Sim and E. W. Nester. 1996. The sensing of plant signal molecules by Agrobacterium: genetic evidence for direct recognition of phenolic inducers by the VirA protein. Gene. 179:83–88.
38. Mantis, N. and S. C. Winans. 1992. The *Agrobacterium tumefaciens* vir gene transcriptional activator virG is transcriptionally induced by acidic pH and other stress stimuli. J. Bacteriol. 174:1189–1196.
39. Messens, E., A. Lenearts, M. M. Van and R. W. Hedges. 1985. Genetic basis for opine secretion from crown gall tumor cells. Mol. Gen. Genet. 25:344–348.
40. Miller, J. H. 1972. Experiments in Molecular genetics. Cold Spring Harbor Laboratory Press, Cold Spring Harbor, N.Y.
41. Murakami, K, M. Kimura, J. T. Owens, C. F. Meares and A. Ishihama. 1997. The two α subunits of *Escherichia coli* RNAP are asymmetrically arranged and contact different halves of the DNA upstream elements. Proc. Natl. Acad. Sci. USA. 94:1709–1714.
42. Nio, W., Y. Kim, G. Tau, T. Heyduk and R. H. Ebright. 1996. Transcriptional activation at Class II CAP-dependent promoters two interactions between CAP and RNAP. Cell. 87:1123–1134.
43. Pan, S. Q., T. Charles, S. Jin, Z. L. Wu and E. W. Nester. 1993. Preformed dimeric state of the sensor protein VirA is involved in plant-Agrobacterium signal transduction. Proc. Natl. Acad. Sci. USA. 90:9939–9943.
44. Pazour, G. J. and A. Das. 1990. Characterization of the VirG binding site of *Agrobacterium tumefaciens*. Nucleic Acids Res. 18:6909–6913.
45. Pazour, G. J., C. N. Ta and A. Das. 1992. Constitutive mutations of *Agrobacterium tumefaciens* transcriptional activator virG. J. Bacteriol. 174:4169–4174.
46. Peacock, A. C. and C. W. Dingrman. 1968. Molecular weight estimation and separation of ribonucleic acid by electrophoresis in agarose-acrylamide gels. Biochemistry. 7:668–674.
47. Ross, W. K., K. Gosnick, J. Salomon, K. Igarashi, C. Zou, A. Ishihama, K. Severinov and R. L. Gourse. 1993. A third recognition element in bacterial promoters: DNA binding by the α subunit of RNAP. Science. 262:1407–1413.
48. Sambrook, J., E. F. Fritsch and T. Maniatis. 1989. Molecular cloning: a laboratory manual, $2^{nd}$ ed. Cold Spring Harbor Laboratory Press, Cold Spring Harbor, N.Y.
49. Savery, N. J., G. S. Lloyd, M. Kainz, T. Gaal., W. Ross, R. H. Ebright, R. L. Gourse and S. J. Busby. 1998. Transcription activation at Class II CRP-dependent promoters: identification of determinants in the C-terminal domain of the RNAP α subunit. EMBO J. 17:3439–3447.
50. Segal, G. and E. Z. Ron. 1993. Cloning, sequencing and transcriptional analysis of the gene coding for the vegetative sigma factor of *Agrobacterium tumefaciens*. J. Bacteriol. 175:3026–3030.
51. Severinov, K., M. Sushko, A. Goldfarb and V. Nikiforov. 1993. Rifampicin region revisited. New rifampicin-resistant and streptolydigin-resistant mutants in the beta subunit of *Escherichia coli* RNAP. J. Biol. Chem. 268:14820–14825.
52. Shimoda, N., A. Toyoda-Yamamoto, J. Nagamine, S. Usami, M. Katayama, Y. Sakagami and Y. Machida. 1990. Control of expression of Agrobacterium vir genes by synergistic actions of phenolic signal molecules and monosaccharides. Proc. Natl. Acad. Sci. USA. 87:6684–6688.
53. Stachel, S. E., G. An. C. Flores and E. W. Nester. 1985. A Tn3 lacZ transposon for the random generation of beta-galactosidase gene fusions: application to the analysis of gene expression in Agrobacterium. EMBO J. 4:891–898.
54. Stachel, S. E., E. W. Nester and P. C. Zambryski. 1986. A plant cell factor induces *Agrobacterium tumefaciens* vir gene expression. Proc. Natl. Acad. Sci. USA. 83:379–383.
55. Tang, H., K. Severinov, A. Goldfarb and R. H. Ebright. 1995. Rapid RNA polymerse genetics: one-day, no-column preparation of reconstituted recombinant

*Escherichia coli* RNAP. Proc. Natl. Acad. Sci. USA. 92:4902–4906.
56. Tao, K., C. Zou, N. Fujita and A. Ishihama. 1995. Mapping of the OxyR protein contact site in the C-terminal region of RNAP α subunit. J. Bacteriol. 177:6740–6744.
57. Thomashow, M. F., S. Hugly, W. G. Buchholz and L. S. Thomashow. 1986. Molecular basis for the auxin-independent phenotype of crown gall tumor tissues. Science. 231:616–618.
58. Watson, B., T. C. Currier, M. P. Gordon, M. D. Chilton and E. W. Nester. 1975. Plasmid required for virulence of *Agrobacterium tumefaciens*. J. Bacteriol. 123:255–264.
59. Williams, S. M., N. J. Savery, S. J. W. Busby and H. J. Wing. 1997. Transcription activation at class 1 FNR-dependent promoters: identification of the activating surface of FNR and the corresponding contact site in the C-terminal domain of the RNAP α subunit. Nucleic Acids Res. 25:4028–4034.
60. Winans, S. C., P. R. Ebert, S. E. Stachel, M. P. Gordon and E. W. Nester. 1986. A gene essential for Agrobacterium virulence is homologous to a family of positive regulatory loci. Proc. Natl. Acad. Sci. USA. 83:8278–8282.
61. Winans, S. C., R. A. Kerstetter and E. W. Nester. 1988. Transcriptional regulation of the virA and virG genes of *Agrobacterium tumefaciens*. J. Bacteriol. 170:4047–4054.
62. Winans, S. C. 1992. Two-way chemical signaling in agrobacterium-plant interactions. Microbiol. Rev. 56:12–31.
63. Zhang, G. and S. A. Darst. 1998. Structure of the *Escherichia coli* RNAP α subunit amino-terminal domain. Science. 281:262–266.
64. Zhou, Y., Merkel, T. J. and R. H. Ebright. 1994. Characterization of the activating region of *Escherichia coli* catabolite gene activator protein (CAP) II. Role at class I and class II CAP-dependent promoters. J. Mol. Biol. 243:603–610.
65. Costacurta and Vandealeydon 1995. Crit. Rev. Microbiol. 21: 1–18.
66. Pueppte. 1996. Crit. Rev. Biochem 16: 1–51.
67. Cook et al. 1995. Proc. Natl. Acad, Sci, USA 92: 4197–4201.
68. Molecular Cloning, A Laboratory Manual, $2^{nd}$ Ed. (1989) Sambrook et al., Cold Spring Harbor Laboratory Press.

TABLE 1

Bacterial Strains and plasmids used in this study

| Strain or plasmid | Genotype or phenotype | Source |
|---|---|---|
| *E. Coli* | | |
| DH5α | recA endAI hsdR17 suspE4 gyrA96 reLAl (lacZYA-argF)U169 (80dlacZ M15) | (56) |
| MC4100 | F' araD139 (argF-kac)U169 rpsL150 relA fib5301 ptsf25deoC1 | (57) |
| HN317 | rpoA112$^{ts}$St$^r$ | (58) |
| Plasmids | | |
| pGP159 | virA. virG & virBp::lacZ; IncP, Ap$^r$,Tc$^r$ | (59) |
| pSM234acd | virA & virBp::lacZ: IncP. Km$^r$ | (45) |
| pLG2 | lacp::virG(N54D) & virBp::lacZ; IncP, AP$^r$Tc$^r$ | This study |
| PSL107 | lacp::virG & virBp::lacZ:IncW, AP$^r$Tc$^r$ | This study |
| pPC401(N54D) | lacp::virG(N54D) in pTZ18R.Ap$^r$ | This study |
| pSY215 | virBp::lacZ & lacp::virG(N54D); IncW, Gm$^r$ | This study |
| pVK102 | Cosmid cloning vector; IncP, Km$^r$, Tc$^r$ | (60) |
| pTZ18R/pTZ19R | Cloning vector; ColE1.Ap$^r$ | USB |
| pBK2 | pVK102 with 25 Kb chromosomal insert from *A. tumefaciens* strain A136, Tc$^r$ | This Study |
| pBKS2-2 | pTZ18R with 7.1 Kb Sau3A insert from pBK2 | This study |
| pBX4.1 | pTZ18R with 4.3 Kb BamHI-XbaI insert from pBKS2-2 | This study |
| pBKS7.0 | pTZ18R with 4.2 Kb Sau3A-Sa/I insert from pBKS2-2 | This study |
| pBKE4.8 | pTZ18R with 1.7 Kb EcoRI-Sau3A insert from pBKS2-2 | This study |
| pPS1.3R | pTZ18R with 1.3 Kb PstI-StuI insert from pBKS2-2 | This study |
| pPS1.3 | pTZ19R with 1.3 Kb PstI-StuI insert from pBKS2-2 | This study |
| pZL-2 | Overproducer of *A. tumefaciens* His-RpoA: Ap$^r$ | This study |
| pECH4 | Overproducer of *E. Coli* HIS-RpoA.Ap$^r$ | This study |
| pH098 | lacp::rpoA of *A. tumefaciens* from pPS1.3: IncW.Km$^r$ | This study |

TABLE 2

RpoA mediated expression of virBP::IacZ fusion in *E. coli* MC4100 containing virG$^{test}$

| | LB medium | | MG/L medium | |
|---|---|---|---|---|
| Constructs | β-Galacto-sidase[b] | Fold Activation[c] | β-Galacto-sidase[b] | Fold Activation |
| pBK102 | 2.46 | NA | 2.35 | NA |
| pBK2 | 5.2 | 2.11 X | 6.56 | 2.79 X |
| pTZ18R | 2.24 | NA | 2.51 | NA |
| pBKS2-2 | 13.67 | 6.1 X | 7.25 | 2.89 X |
| pBX4.1 | 26.42 | 11.8 X | 8.11 | 3.23 X |
| pBKS7.0 | 1.68 | 0.75 X | 2.46 | 0.98 X |
| pBKE4.8 | 2.36 | 1.05 X | 1.63 | 0.65 X |
| pBP3.0 | 5.45 | 2.43 X | 2.83 | 1.13 X |
| pPS1.3R | 2.13 | 0.95 X | 1.71 | 0.68 X |
| pPS1.3 | 76.14 | 40.0 X | 37.69 | 15.0 X |

The virBp::lacZ expression assays were carried out in LB and MG/L medium for 16 hours as described in the text, IPTG was added at a final concentration of 1 mM. *E. coli* MC4100 containing pSY215 (virG$^{con}$ + virBp::lacZ.
[b]Values are the average of three replicates.
[c]Values indicate an increase or decrease in activity compared to the appropriate control vector.
NA, Not Applicable.

TABLE 3

β-galactosidase activities

| *E.coli* strain MC4100(pSY215) plus plasmid shown in right | pPS1.3 | pAD8 | pQE31 |
|---|---|---|---|
| β-galactosidase in Miller Units* | 140 (+/−25) | 4 (+/−1) | 3 (+/−2) |

*Miller Units = Defined in Ref. 68.

What is claimed is:

1. An isolated nucleic acid molecule encoding the complete α subunit of an RNA polymerase (RNAP) of Agrobacterium, wherein the amino acid sequence of said α subunit is depicted in FIG. 2A (SEQ ID NO: 1).

2. An isolated nucleic acid molecule of claim 1 comprising the nucleic acid sequence as depicted in FIG. 2B (SEQ ID NO:2).

3. A hybrid nucleic acid molecule for the expression of at least one heterologous gene in an E. coli host cell, wherein said hybrid nucleic acid molecule comprises a first nucleic acid sequence encoding at least a portion of the α subunit of an E. coli RNA polymerase (RNAP), and a second nucleic acid sequence encoding at least a portion of the α subunit of an RNAP obtained from Agrobacterium as depicted in SEQ ID NO: 1, wherein said portion of the amino acid sequence as depicted in SEQ ID NO: 1 comprises at least amino acid residues 157 to 336 of SEQ ID NO: 1, or comprises less than amino acid residues 157 to 336 of SEQ ID NO: 1 but does comprise amino acid residues 329 to 336, and further wherein said hybrid nucleic acid encodes a hybrid α-subunit of RNAP.

4. The hybrid nucleic acid molecule of claim 3, wherein said second nucleic acid sequence encodes the amino acid sequence as depicted in SEQ ID NO:1.

5. A nucleic acid construct comprising a nucleic acid molecule of claim 3 operably linked to a promoter.

6. A vector comprising the nucleic acid construct of claim 5.

7. A host cell comprising a nucleic acid construct of claim 5 or a vector of claim 6, wherein said promoter is operable in said host cell.

8. A host cell of claim 7, further comprising at least one heterologous gene operably linked to a promoter.

9. A host cell of claim 8, wherein said heterologous gene and promoter are contained in a vector.

10. A method of expressing at least one heterologous gene in an E. coli host cell, comprising:

(a) transforming said E. coli host cell with either (i) a nucleic acid molecule encoding a complete α subunit of an RNA polymerase obtained from Agrobacterium as depicted in SEQ ID NO: 1, or (ii) a hybrid nucleic acid molecule comprising a first nucleic acid sequence encoding at least a portion of the α subunit of an E. coli RNA polymerase operatively linked to a second nucleic acid sequence encoding at least a portion of the α subunit depicted in SEQ ID NO: 1, wherein said portion of the α subunit depicted in SEQ ID NO: 1 comprises at least amino acid residues 157 to 336 of SEQ ID NO: 1, or comprises less than amino acid residues 157 to 336 of SEQ ID NO: 1 but does comprise amino acid residues 329–336;

wherein the nucleic acid molecule of (i) or (ii) is operatively linked to a promoter, and wherein the host cell comprises at least one heterologous coding sequence operatively linked to a promoter obtained from Agrobacterium tumefaciens, and (b) culturing said transformed host cell under conditions wherein at least one heterologous gene is expressed in said host cell.

11. The method of claim 10, further comprising transforming said host cell with at least one gene encoding a heterologous transcriptional regulator obtained from the same genus as the source of the heterologous gene.

12. The method of claim 11, wherein said transcriptional regulator is a transcriptional activator that interacts with said α subunit of the RNAP to enhance the expression of said heterologous gene.

13. The method of claim 10, wherein said heterologous gene comprises multiple genes or operons in the same metabolic pathway.

14. The method of claim 10, wherein said nucleic acid molecule and said at least one heterologous gene are contained in at least one vector.

15. The method of claim 10, wherein said host cell is transformed with a vector comprising the nucleic acid molecule and with at least one vector comprising at least one heterologous gene.

16. The method of claim 10, wherein the nucleic acid molecule encoding at least a portion of the α subunit of an RNAP is obtained from *Agrobacterium tumefaciens*.

17. The method of claim 10, wherein the nucleic acid a molecule is depicted in SEQ ID NO: 2.

18. The method of claim 10, wherein said at least a portion of the nucleic acid sequence is depicted in SEQ ID NO:2.

* * * * *

SEQUENCE LISTING

<160> NUMBER OF SEQ ID NOS: 9

<210> SEQ ID NO 1
<211> LENGTH: 336
<212> TYPE: PRT
<213> ORGANISM: Agrobacterium tumefaciens

<400> SEQUENCE: 1

Met Ile Gln Lys Asn Trp Gln Glu Leu Ile Lys Pro Asn Lys Val Glu
1               5                   10                  15

Phe Thr Ser Ser Ser Arg Thr Lys Ala Thr Leu Val Ala Glu Pro Leu
            20                  25                  30

Glu Arg Gly Phe Gly Leu Thr Leu Gly Asn Ala Leu Arg Arg Val Leu
        35                  40                  45

Leu Ser Ser Leu Arg Gly Ala Ala Val Thr Ala Val Gln Ile Asp Gly
50                  55                  60

Val Leu His Glu Phe Ser Ser Ile Pro Gly Val Arg Glu Asp Val Thr
65                  70                  75                  80

Asp Ile Val Leu Asn Ile Lys Glu Ile Ala Ile Lys Met Asp Gly Asp
                85                  90                  95

Asp Ser Lys Arg Met Val Val Arg Lys Gln Gly Pro Gly Ser Val Thr
            100                 105                 110

Ala Gly Asp Ile Gln Thr Val Gly Asp Ile Glu Ile Leu Asn Pro Asp
        115                 120                 125

His Val Ile Cys Thr Leu Asp Glu Gly Ala Glu Ile Arg Met Glu Phe
130                 135                 140

Thr Val Asn Asn Gly Lys Gly Tyr Val Pro Ala Glu Arg Asn Arg Ala
145                 150                 155                 160

Glu Asp Ala Pro Ile Gly Leu Ile Pro Val Asp Ser Leu Tyr Ser Pro
                165                 170                 175

Val Lys Lys Val Ser Tyr Lys Val Glu Asn Thr Arg Glu Gly Gln Val
            180                 185                 190

Leu Asp Tyr Asp Lys Leu Ile Met Thr Ile Glu Thr Asn Gly Ser Val
        195                 200                 205

Ser Gly Glu Asp Ala Val Ala Phe Ala Ala Arg Ile Leu Gln Asp Gln
210                 215                 220

Leu Gly Val Phe Val Asn Phe Asp Glu Pro Gln Lys Glu Ala Glu Glu
225                 230                 235                 240

Glu Ser Val Thr Glu Leu Ala Phe Asn Pro Ala Leu Leu Lys Lys Val
                245                 250                 255

Asp Glu Leu Glu Leu Ser Val Arg Ser Ala Asn Cys Leu Lys Asn Asp
            260                 265                 270

Asn Ile Val Tyr Ile Gly Asp Leu Ile Gln Lys Thr Glu Ala Glu Met
        275                 280                 285

Leu Arg Thr Pro Asn Phe Gly Arg Lys Ser Leu Asn Glu Ile Lys Glu
290                 295                 300

Val Leu Ala Ser Met Gly Leu His Leu Gly Met Glu Val Pro Ala Trp
305                 310                 315                 320

Pro Pro Glu Asn Ile Glu Asp Leu Ala Lys Arg Tyr Glu Asp Gln Tyr
                325                 330                 335

<210> SEQ ID NO 2
<211> LENGTH: 1692
<212> TYPE: DNA

<213> ORGANISM: Agrobacterium tumefaciens

<400> SEQUENCE: 2

```
aacacggcat gaagtcgctt gaagtcgaag tttgcggtcc gggttccggt cgtgaatcgg      60
cacttcgcgc tctgcaggct gccggtttca tgatcacttc cattcgcgac gccgatcccg     120
cacaacggtt gccgtccgcg caagaagcgc gcgtctgac gcgaccgtgg ttcggaaatt      180
ccgcctttcc ttcggtctgg cggaattttc gtgtatctgg cgtgtgcgcg tcgatttcga     240
tcgacggact tgcgctcaag aacccactga tgaaccactg aattaggttc ctctcggtgt     300
tttcatgctc ggtccgtcac gattggatgg tggcggcgaa cggaaggttt aaagatgatt     360
cagaagaact ggcaggaact tatcaagccg aacaaggtcg agttcacctc gtccagccgc     420
accaaggcaa ctctggttgc cgagccgctg gagcgtggtt cggtcttac cctcggcaac      480
gcgctgcgcc gcgttctgtt gtcttctctg cgtggtgccg ctgtaacggc cgtgcagatc     540
gacggtgtcc tgcacgaatt ctcctccatc cccggcgttc gggaagatgt gacggatatc     600
gtgctcaaca tcaaggaaat cgccatcaag atggatggtg acgattccaa gcgcatggtc     660
gtgcgcaagc agggtccggg ttcggtaacc gctggtgaca tccagacggt tggcgacatc     720
gagatcctga accccgacca cgtgatctgc acgctcgatg aaggcgctga atccgcatg      780
gaattcaccg tcaacaacgg caaggggttac gtaccggctg agcgcaaccg cgcggaagat     840
gccctatcg gcctcattcc ggtggacagc ctctattctc cggtcaagaa agtgtcctac      900
aaggtggaaa cacccgtga aggtcaggtt ctcgactatg caagctgat catgacgatc       960
gagaccaacg gttcggtttc cggcgaagac gccgttgcct tcgccgctcg cattcttcag    1020
gaccagctgg gcgtcttcgt caacttcgac gagccgcaga aggaagcaga agaagaatcg    1080
gttactgaac tcgcgttcaa cccggcgctt ctcaagaagg tcgacgagct cgaactgtca    1140
gttcgttcgg caaactgcct gaagaacgac aacatcgttt atatcggcga cctgatccag    1200
aagaccgaag ccgaaatgct ccgcacgccg aactttggtc gcaagtcgct gaacgaaatc    1260
aaggaagttc tcgcttccat gggtctgcac ctcggcatgg aagtgccggc atggccgcct    1320
gagaacatcg aagatctcgc aaagcgttac gaagaccaat actaacaaac aagaaggcag    1380
acctttaaaga ctgcctttcc ccgtcaaaca gcagataagt catctgcatg tgccaggaaa   1440
cggcaggcct taaagaaggc acctgcgtag aaggagaata gcaatgcgcc acggtaattc    1500
aggccgcaag ctcaatagaa ccgccagcca ccgcaaggca atgtttgcca acatggctgc    1560
ttcgctcatc acccatgagc agatcgtcac caccttccg aaggcgaagg aaatccgtcc      1620
gatcgtcgag cgtctcgtga cgctgggcaa gcgcggcgac ctgcacgctc gtcgtcaggc    1680
gatctcgcag at                                                        1692
```

<210> SEQ ID NO 3
<211> LENGTH: 327
<212> TYPE: PRT
<213> ORGANISM: Escherichia coli

<400> SEQUENCE: 3

```
Met Gln Gly Ser Val Thr Glu Phe Leu Lys Pro Arg Leu Val Ile Glu
1               5                  10                  15

Gln Val Ser Ser Thr His Ala Lys Val Thr Leu Glu Pro Leu Glu Arg
            20                  25                  30

Gly Phe Gly Glu Thr Leu Gly Asn Ala Leu Arg Arg Ile Leu Leu Ser
        35                  40                  45
```

```
Ser Met Phe Gly Cys Ala Val Thr Glu Val Glu Ile Asp Gly Val Leu
 50                  55                  60

His Glu Tyr Ser Thr Lys Glu Gly Val Gln Glu Asp Ile Leu Glu Ile
 65                  70                  75                  80

Leu Leu Asn Leu Lys Gly Leu Ala Val Arg Val Gln Gly Lys Asp Glu
                 85                  90                  95

Val Ile Leu Thr Leu Asn Lys Ser Gly Ile Gly Pro Val Thr Ala Ala
                100                 105                 110

Asp Ile Thr His Gly Asp Val Glu Ile Val Lys Pro Gln His Val Ile
                115                 120                 125

Cys His Leu Thr Asp Glu Asn Ala Ser Ile Ser Met Arg Ile Lys Val
        130                 135                 140

Gln Arg Gly Arg Gly Tyr Val Pro Ala Ser Thr Arg Ile His Ser Glu
145                 150                 155                 160

Glu Asp Glu Arg Pro Ile Gly Arg Leu Leu Val Asp Ala Cys Tyr Ser
                165                 170                 175

Pro Val Glu Arg Ile Ala Tyr Asn Val Glu Ala Ala Arg Val Glu Gln
                180                 185                 190

Arg Thr Asp Leu Asp Lys Leu Val Ile Glu Met Glu Thr Thr Gly Thr
        195                 200                 205

Ile Asp Pro Glu Glu Ala Ile Arg Arg Ala Ala Thr Ile Leu Ala Glu
210                 215                 220

Gln Leu Glu Ala Phe Val Asp Leu Arg Asp Val Arg Gln Pro Glu Val
225                 230                 235                 240

Lys Glu Glu Lys Pro Glu Phe Asp Pro Ile Leu Leu Arg Pro Val Asp
                245                 250                 255

Asp Leu Glu Leu Thr Val Arg Ser Ala Asn Cys Leu Lys Ala Glu Ala
                260                 265                 270

Ile His Tyr Ile Gly Asp Leu Val Gln Arg Thr Glu Val Glu Leu Leu
                275                 280                 285

Lys Thr Pro Asn Leu Gly Lys Lys Ser Leu Thr Glu Ile Lys Asp Val
        290                 295                 300

Leu Ala Ser Arg Gly Leu Ser Leu Gly Met Arg Leu Glu Asn Trp Pro
305                 310                 315                 320

Pro Ala Ser Ile Ala Asp Glu
                325

<210> SEQ ID NO 4
<211> LENGTH: 24
<212> TYPE: DNA
<213> ORGANISM: Escherichia coli

<400> SEQUENCE: 4
ccaaagagag gatccaatgc aggg                                    24

<210> SEQ ID NO 5
<211> LENGTH: 25
<212> TYPE: DNA
<213> ORGANISM: Escherichia coli

<400> SEQUENCE: 5
ccttaacctg ggatccggtt actcg                                   25

<210> SEQ ID NO 6
<211> LENGTH: 26
<212> TYPE: DNA
<213> ORGANISM: Agrobacterium tumefaciens
```

-continued

```
<400> SEQUENCE: 6
ggaaggatcc aagatgattc agaaga                                                26

<210> SEQ ID NO 7
<211> LENGTH: 27
<212> TYPE: DNA
<213> ORGANISM: Agrobacterium tumefaciens

<400> SEQUENCE: 7
cctggaatcc tgcagatgac ttatctg                                               27

<210> SEQ ID NO 8
<211> LENGTH: 22
<212> TYPE: DNA
<213> ORGANISM: Unknown
<220> FEATURE:
<223> OTHER INFORMATION: Primer

<400> SEQUENCE: 8
ttccacggtg acgcatcgaa tg                                                    22

<210> SEQ ID NO 9
<211> LENGTH: 29
<212> TYPE: DNA
<213> ORGANISM: Unknown
<220> FEATURE:
<223> OTHER INFORMATION: Primer

<400> SEQUENCE: 9
ccccgatctc ttaaacatac cttatctcc                                             29
```